United States Patent
Brown et al.

(10) Patent No.: US 11,111,532 B2
(45) Date of Patent: Sep. 7, 2021

(54) METHOD OF CHARACTERIZING A TARGET RIBONUCLEIC ACID (RNA) COMPRISING FORMING A COMPLEMENTARY POLYNUCLEOTIDE WHICH MOVES THROUGH A TRANSMEMBRANE PORE

(71) Applicant: Oxford Nanopore Technologies Ltd., Oxford (GB)

(72) Inventors: Clive Gavin Brown, Cambridge (GB); Daniel John Turner, Oxford (GB); James White, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 445 days.

(21) Appl. No.: 15/028,637

(22) PCT Filed: Oct. 17, 2014

(86) PCT No.: PCT/GB2014/053121
§ 371 (c)(1),
(2) Date: Apr. 11, 2016

(87) PCT Pub. No.: WO2015/056028
PCT Pub. Date: Apr. 23, 2015

(65) Prior Publication Data
US 2016/0251710 A1    Sep. 1, 2016

(30) Foreign Application Priority Data

Oct. 18, 2013 (GB) ..................................... 1318465

(51) Int. Cl.
*C12Q 1/6869* (2018.01)
*C12Q 1/6883* (2018.01)
*G01N 27/416* (2006.01)

(52) U.S. Cl.
CPC ......... *C12Q 1/6869* (2013.01); *C12Q 1/6883* (2013.01); *G01N 27/4166* (2013.01);
(Continued)

(58) Field of Classification Search
None
See application file for complete search history.

(56) References Cited

U.S. PATENT DOCUMENTS 5,576,204 A   11/1996   Blanco et al.
5,656,462 A * 8/1997   Keller ............... C12N 15/1006
                                                435/91.2
(Continued)

FOREIGN PATENT DOCUMENTS

CN   102430153 A   5/2012
CN   103827320 A   5/2014
(Continued)

OTHER PUBLICATIONS

Sequence Listing for U.S. Appl. No. 61/511,436, filed Jul. 25, 2011. (Year: 2011).*

(Continued)

*Primary Examiner* — Samuel C Woolwine
(74) *Attorney, Agent, or Firm* — Wolf, Greenfield & Sacks, P.C.

(57) ABSTRACT

The invention relates to a new method of characterising a target ribonucleic acid (RNA) involving forming a complementary polynucleotide. The method uses a transmembrane pore.

33 Claims, 5 Drawing Sheets
Specification includes a Sequence Listing.

(52) U.S. Cl.
CPC .. *C12Q 2600/118* (2013.01); *C12Q 2600/158* (2013.01); *C12Q 2600/178* (2013.01)

(56) References Cited

U.S. PATENT DOCUMENTS

| | | | |
|---|---|---|---|
| 6,426,231 | B1 | 7/2002 | Bayley et al. |
| 6,617,113 | B2* | 9/2003 | Deamer ............ C12N 15/1003 435/285.2 |
| 8,105,846 | B2 | 1/2012 | Bayley et al. |
| 8,828,208 | B2 | 9/2014 | Canas et al. |
| 9,057,102 | B2 | 6/2015 | Turner et al. |
| 9,546,400 | B2 | 1/2017 | Turner et al. |
| 9,551,023 | B2 | 1/2017 | Turner et al. |
| 9,556,480 | B2 | 1/2017 | Turner et al. |
| 9,678,056 | B2 | 6/2017 | Turner et al. |
| 9,738,929 | B2 | 8/2017 | Turner et al. |
| 9,995,728 | B2 | 6/2018 | Fordham et al. |
| 10,480,026 | B2 | 11/2019 | Garalde et al. |
| 10,739,341 | B2 | 8/2020 | Turner et al. |
| 2002/0197618 | A1 | 12/2002 | Sampson |
| 2003/0080042 | A1 | 5/2003 | Barth et al. |
| 2003/0199471 | A1 | 10/2003 | Taira et al. |
| 2004/0029158 | A1* | 2/2004 | Olson .................... C07H 21/04 435/6.17 |
| 2004/0058378 | A1 | 3/2004 | Kong et al. |
| 2004/0203037 | A1* | 10/2004 | Lo ....................... C12Q 1/6883 435/6.17 |
| 2005/0014162 | A1 | 1/2005 | Barth et al. |
| 2006/0014172 | A1 | 1/2006 | Muller et al. |
| 2006/0063171 | A1* | 3/2006 | Akeson ............ B01L 3/502707 435/6.11 |
| 2007/0190543 | A1 | 8/2007 | Livak |
| 2007/0224613 | A1 | 9/2007 | Strathmann |
| 2010/0035260 | A1* | 2/2010 | Olasagasti ................ C25B 3/10 435/6.16 |
| 2010/0092960 | A1* | 4/2010 | Fehr ..................... C12Q 1/6869 435/6.11 |
| 2010/0111922 | A1* | 5/2010 | Gibori ................ A01K 67/0276 424/94.4 |
| 2010/0196203 | A1 | 8/2010 | Sanghera et al. |
| 2010/0291548 | A1 | 11/2010 | Sharaf et al. |
| 2010/0304991 | A1 | 12/2010 | Brown |
| 2011/0118187 | A1 | 5/2011 | Sullenger et al. |
| 2011/0120871 | A1 | 5/2011 | Reid et al. |
| 2011/0121840 | A1 | 5/2011 | Sanghera et al. |
| 2011/0177498 | A1 | 7/2011 | Clarke et al. |
| 2011/0229877 | A1 | 9/2011 | Jayasinghe et al. |
| 2011/0250705 | A1 | 10/2011 | Polonsky et al. |
| 2011/0263459 | A1 | 10/2011 | Borer et al. |
| 2011/0287557 | A1 | 11/2011 | Zhang et al. |
| 2012/0025414 | A1 | 2/2012 | Schmidt |
| 2012/0058468 | A1 | 3/2012 | Mckeown |
| 2012/0100530 | A1 | 4/2012 | Moysey et al. |
| 2012/0107802 | A1 | 5/2012 | Stoddart et al. |
| 2012/0322679 | A1 | 12/2012 | Brown et al. |
| 2013/0116130 | A1* | 5/2013 | Fu ....................... C12Q 1/6837 506/4 |
| 2014/0051069 | A1 | 2/2014 | Jayasinghe et al. |
| 2014/0174927 | A1* | 6/2014 | Bashir .................. C12Q 1/6827 204/452 |
| 2014/0186823 | A1 | 7/2014 | Clarke et al. |
| 2014/0234834 | A1 | 8/2014 | Di Pasquale et al. |
| 2014/0296083 | A1 | 10/2014 | Brown et al. |
| 2015/0008126 | A1 | 1/2015 | Maglia et al. |
| 2015/0031020 | A1 | 1/2015 | Jayasinghe et al. |
| 2015/0152492 | A1 | 6/2015 | Brown et al. |
| 2015/0177237 | A1 | 6/2015 | Turner et al. |
| 2015/0247183 | A1 | 9/2015 | Turner et al. |
| 2015/0301015 | A1 | 10/2015 | Fordham et al. |
| 2016/0010147 | A1 | 1/2016 | Heron et al. |
| 2016/0257942 | A1 | 9/2016 | Bruce et al. |
| 2017/0253923 | A1 | 9/2017 | Garalde et al. |
| 2020/0063199 | A1 | 2/2020 | Garalde et al. |

FOREIGN PATENT DOCUMENTS

| | | | |
|---|---|---|---|
| JP | 2010-524436 A | 7/2010 | |
| JP | 2014-506575 A | 3/2014 | |
| WO | 2000/028312 | 5/2000 | |
| WO | WO 2005/124888 | 12/2005 | |
| WO | WO 2006/100484 | 9/2006 | |
| WO | WO 2008/102120 | 8/2008 | |
| WO | WO 2008/102121 | 8/2008 | |
| WO | WO 2008/124107 | 10/2008 | |
| WO | WO 2009/035647 | 3/2009 | |
| WO | WO 2009/046149 | 6/2009 | |
| WO | WO 2009/077734 A2 | 6/2009 | |
| WO | WO 2010/004265 | 1/2010 | |
| WO | WO 2010/004273 | 1/2010 | |
| WO | WO 2010/086603 | 8/2010 | |
| WO | WO 2010/109197 | 9/2010 | |
| WO | WO 2010/122293 | 10/2010 | |
| WO | WO 2011/067559 | 6/2011 | |
| WO | WO 2011/103424 A2 | 8/2011 | |
| WO | WO 2012/009578 | 1/2012 | |
| WO | WO 2012/033524 | 3/2012 | |
| WO | WO 2012/088339 A2 | 6/2012 | |
| WO | WO 2012/107778 A2 | 8/2012 | |
| WO | WO 2012/129242 A2 | 9/2012 | |
| WO | WO 2012/164270 A1 | 12/2012 | |
| WO | WO 2013/014451 A1 | 1/2013 | |
| WO | WO-2013014451 A1 * | 1/2013 | ........... C12Q 1/6869 |
| WO | WO 2013/057495 A2 | 4/2013 | |
| WO | WO 2013/098561 A1 | 7/2013 | |
| WO | WO 2013/098562 A2 | 7/2013 | |
| WO | WO 2013/121201 | 8/2013 | |
| WO | 2013/142939 A1 | 10/2013 | |
| WO | WO 2013/153359 A1 | 10/2013 | |
| WO | WO 2014/013259 A1 | 1/2014 | |
| WO | WO 2014/013260 A1 | 1/2014 | |
| WO | WO 2014/013262 A1 | 1/2014 | |
| WO | WO 2014/041337 A1 | 3/2014 | |
| WO | WO 2014/072703 A1 | 5/2014 | |
| WO | WO 2014/135838 A1 | 9/2014 | |
| WO | WO 2015/055981 A2 | 4/2015 | |
| WO | WO 2015/056028 A1 | 4/2015 | |
| WO | WO 2015/110777 A1 | 7/2015 | |

OTHER PUBLICATIONS

Office action for European application EP 14792535, dated Sep. 4, 2020. (Year: 2020).*
Garcia-Manero et al. Chronic myelogenous leukemia: a review and update of therapeutic strategies. Cancer 98(3):437-457. (Year: 2003).*
Shin et al., The replicative helicases of bacteria, archaea, and eukarya can unwind RNA-DNA hybrid substrates. J Biol Chem. Sep. 15, 2006;281(37):26914-21. Epub Jul. 7, 2006.
[No Author Listed] Aptamer. Retrieved from Wikipedia.com on Nov. 3, 2019. 14 pages.
[No Author Listed] Aptamer. Retrieved from Meriam-Webster.com on Nov. 13, 2019. 5 pages.
Abe et al., Biosensors—Emerging Materials and Applications. Chapter 12: Aptamer Sensors Combined with Enzymes for Highly Sensitive Detection. IntechOpen. 2011. doi: 10.5772/19708. 19 pages.
Manrao et al., Nucleotide discrimination with DNA immobilized in the MspA nanopore. PLoS One. 2011;6(10):e25723. doi: 10.1371/journal.pone.0025723. Epub Oct. 4, 2011.
Nimjee et al., Aptamers: an emerging class of therapeutics. Annu Rev Med. 2005;56:555-83.
Rusconi et al., RNA aptamers as reversible antagonists of coagulation factor IXa. Nature. Sep. 5, 2002;419(6902):90-4.
Song et al., Aptamers and their biological applications. Sensors (Basel). 2012;12(1):612-31. doi: 10.3390/s120100612. Epub Jan. 9, 2012.
Actis et al., Reversible thrombin detection by aptamer functionalized STING sensors. Biosens Bioelectron. Jul. 15, 2011;26(11):4503-7. doi: 10.1016/j.bios.2011.05.010. Epub May 12, 2011.
Altschul et al., Basic local alignment search tool. J Mol Biol. Oct. 5, 1990;215(3):403-10.

(56) References Cited

OTHER PUBLICATIONS

Altschul, A protein alignment scoring system sensitive at all evolutionary distances. J Mol Evol. Mar. 1993;36(3):290-300.
Anderson, The clinical plasma proteome: a survey of clinical assays for proteins in plasma and serum. Clin Chem. Feb. 2010;56(2):177-85. doi:10.1373/clinchem.2009.126706. Epub Nov. 2, 2009.
Ayub et al., Individual RNA base recognition in immobilized oligonucleotides using a protein nanopore. Nano Lett. Nov. 14, 2012;12(11):5637-43. doi: 10.1021/nl3027873. Epub Oct. 19 2012.
Barshack et al., Differential diagnosis of hepatocellular carcinoma from metastatic tumors in the liver using microRNA expression. Int J Biochem Cell Biol. Aug. 2010;42(8):1355-62. doi:10.1016/j.biocel.2009.02.021. Epub Mar. 6, 2009.
Berezovski et al., Non-SELEX selection of aptamers. J Am Chem Soc. Feb. 8, 2006;128(5):1410-1.
Bock et al., Selection of single-stranded DNA molecules that bind and inhibit human thrombin. Nature. Feb. 6, 1992;355(6360):564-6.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Chandler et al., Membrane surface dynamics of DNA-threaded nanopores revealed by simultaneous single-molecule optical and ensemble electrical recording. Langmuir. Feb. 3, 2004;20(3):898-905.
Chen et al., Highly sensitive and specific microRNA expression profiling using BeadArray technology. Nucleic Acids Res. Aug. 2008;36(14):e87. doi:10.1093/nar/gkn387. Epub Jun. 25, 2008.
Chen et al., Real-time quantification of microRNAs by stem-loop RT-PCR. Nucleic Acids Res. Nov. 27, 2005;33(20):e179.
Cheng et al., DNA strand transfer catalyzed by vaccinia topoisomerase:ligation of DNAs containing a 3' mononucleotide overhang. Nucleic Acids Res. May 1, 2000;28(9):1893-8.
Cissell et al., Bioluminescence-based detection of microRNA, miR21 in breast cancer cells. Anal Chem. Apr. 1, 2008;80(7):2319-25. doi: 10.1021/ac702577a. Epub Feb. 27, 2008.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Dahl et al., Direct observation of translocation in individual DNA polymerase complexes. J Biol Chem. Apr. 13, 2012;287(16):13407-21. doi:10.1074/jbc.M111.338418. Epub Feb. 29, 2012.
Deamer, Nanopore analysis of nucleic acids bound to exonucleases and polymerases. Annu Rev Biophys. 2010;39:79-90. doi:10.1146/annurev.biophys.093008.131250.
Devereux et al., A comprehensive set of sequence analysis programs for the VAX. Nucleic Acids Res. Jan. 11, 1984;12(1 Pt 1):387-95.
Dong et al., Wza the translocon for *E. coli* capsular polysaccharides defines a new class of membrane protein. Nature. Nov. 9, 2006;444(7116):226-9.
Edwards et al., The role of proteomics in clinical cardiovascular biomarker discovery. Mol Cell Proteomics. Oct. 2008;7(10):1824-37. doi: 10.1074/mcp.R800007-MCP200. Epub Jul. 30, 2008.
Eliseev et al., Molecular Recognition of Nucleotides, Nucleosides, and Sugars by Aminocyclodextrins. J. Am. Chem. Soc., vol. 116:6081-6088 (1994).
Esquela-Kerscher et al., Oncomirs—microRNAs with a role in cancer. Nat Rev Cancer. Apr. 2006;6(4):259-69.
Gilad et al., Serum microRNAs are promising novel biomarkers. PLoS One. Sep. 5, 2008;3(9):e3148. doi:10.1371/journal.pone.0003148.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Grant et al., A facile method for attaching nitroxide spin labels at the 5' terminus of nucleic acids. Nucleic Acids Res. 2007;35(10):e77. Epub May 21, 2007.
Gu et al., Detection of miRNAs with a nanopore single-molecule counter. Expert Rev Mol Diagn. Jul. 2012;12(6):573-84. doi: 10.1586/erm.12.58.
Gu et al., Single molecule sensing by nanopores and nanopore devices. Analyst. Mar. 2010;135(3):441-51. doi: 10.1039/b907735a. Epub Dec. 22, 2009.
Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Ivanov et al., DNA tunneling detector embedded in a nanopore. Nano Lett. Jan. 12, 2011;11(1):279-85. doi: 10.1021/nl103873a. Epub Dec. 6, 2010.
Jacquet et al., Identification of cardiac myosin-binding protein C as a candidate biomarker of myocardial infarction by proteomics analysis. Mol Cell Proteomics. Dec. 2009;8(12):2687-99. doi: 10.1074/mcp.M900176-MCP200. Epub Aug. 31, 2009.
Jiang et al., miR2Disease: a manually curated database for microRNA deregulation in human disease. Nucleic Acids Res. Jan. 2009;37(Database issue):D98-104. doi:10.1093/nar/gkn714. Epub Oct. 15, 2008.
Kankia et al., Folding of the thrombin aptamer into a G-quadruplex with Sr(2+): stability, heat, and hydration. J Am Chem Soc. Nov. 7, 2001;123(44):10799-804.
Keller et al., Toward the blood-borne miRNome of human diseases. Nat Methods. Sep. 4, 2011;8(10):841-3. doi: 10.1038/nmeth.1682.
Khan et al., Quantitative analysis of microRNA in blood serum with protein-facilitated affinity capillary electrophoresis. Anal Chem. Aug. 15, 2011;83(16):6196-201. doi: 10.1021/ac2016213. Epub Jul. 18, 2011.
Kirschner et al., Haemolysis during sample preparation alters microRNA content of plasma. PLoS One. 2011;6(9):e24145. doi: 10.1371/journal.pone.0024145. Epub Sep. 1, 2011.
Kocalka et al., Rapid and efficient DNA strand cross-linking by click chemistry. Chembiochem. May 23, 2008;9(8):1280-5. doi:10.1002/cbic.200800006.
Kolb et al., Click Chemistry: Diverse Chemical Function from a Few Good Reactions. Angew Chem Int Ed Engl. Jun. 1, 2001;40(11):2004-2021.
Kozarewa et al., 96-plex molecular barcoding for the Illumina Genome Analyzer. Methods Mol Biol. 2011;733:279-98. doi: 10.1007/978-1-61779-089-8_20.
Krichevsky et al., A microRNA array reveals extensive regulation of microRNAs during brain development. RNA. Oct. 2003;9(10):1274-81. Erratum in: RNA. Mar. 2004;10(3):551.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Langecker et al., Synthetic lipid membrane channels formed by designed DNA nanostructures. Science. Nov. 16, 2012;338(6109):932-6. doi: 10.1126/science.1225624.
Lee et al., The C. elegans heterochronic gene lin-4 encodes small RNAs with antisense complementarity to lin-14. Cell. Dec. 3, 1993;75(5):843-54.
Lewis et al., Conserved seed pairing, often flanked by adenosines, indicates that thousands of human genes are microRNA targets. Cell. Jan. 14, 2005;120(1):15-20.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Loakes, Survey and summary: The applications of universal DNA base analogues. Nucleic Acids Res. Jun. 15, 2001;29(12):2437-47.
Lu et al., MicroRNA expression profiles classify human cancers. Nature. Jun. 9, 2005;435(7043):834-8.

(56) References Cited

OTHER PUBLICATIONS

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Marathias et al., Structures of the potassium-saturated, 2:1, and intermediate, 1:1, forms of a quadruplex DNA. Nucleic Acids Res. May 1, 2000;28(9):1969-77.
Marusic et al., Solution-state structure of an intramolecular G-quadruplex with propeller, diagonal and edgewise loops . (2012) Nucleic Acids Research, 1-11.
Montal et al., Formation of bimolecular membranes from lipid monolayers and a study of their electrical properties. Proc Natl Acad Sci U S A. Dec. 1972;69(12):3561-6.
Movileanu, Interrogating single proteins through nanopores: challenges and opportunities. Trends Biotechnol. Jun. 2009;27(6):333-41. doi:10.1016/j.tibtech.2009.02.008. Epub Apr. 23, 2009.
Murphy et al., Reliability of real-time reverse-transcription PCR in clinical diagnostics: gold standard or substandard? Expert Rev Mol Diagn. Mar. 2009;9(2):187-97. doi: 10.1586/14737159.9.2.187.
Nasheri et al., An enzyme-linked assay for the rapid quantification of microRNAs based on the viral suppressor of RNA silencing protein p19. Anal Biochem. May 15, 2011;412(2):165-72. doi: 10.1016/j.ab.2011.01.030. Epub Feb. 1, 2011.
Nikolov et al., Behavior of giant vesicles with anchored DNA molecules. Biophys J. Jun. 15, 2007;92(12):4356-68. Epub Mar. 23, 2007.
Pfeiffer et al., Bivalent cholesterol-based coupling of oligonucleotides to lipid membrane assemblies. J Am Chem Soc. Aug. 25, 2004;126(33):10224-5.
Reinhart et al., MicroRNAs in plants. Genes Dev. Jul. 1, 2002;16(13):1616-26. Erratum in: Genes Dev Sep. 1, 2002;16(17):2313.
Rosenfeld et al., MicroRNAs accurately identify cancer tissue origin. Nat Biotechnol. Apr. 2008;26(4):462-9. doi:10.1038/nbt1392. Epub Mar. 23, 2008.
Rotem et al., Protein detection by nanopores equipped with aptamers. J Am Chem Soc. Feb. 8, 2012;134(5):2781-7. doi:10.1021/ja2105653. Epub Jan. 26, 2012.
Sekiguchi et al., Kinetic analysis of DNA and RNA strand transfer reactions catalyzed by vaccinia topoisomerase. J Biol Chem. Jun. 20, 1997;272(25):15721-8.
Shi et al., 5' RACE by tailing a general template-switching oligonucleotide. Biotechniques. Dec. 2000;29(6):1192-5. Erratum in: Biotechniques May 2001;30(5):934.
Shim et al., Single-molecule detection of folding and unfolding of the G-quadruplex aptamer in a nanopore nanocavity. Nucleic Acids Res. Feb. 2009;37(3):972-82. doi: 10.1093/nar/gkn968. Epub Dec. 26, 2008.
Soni et al., Synchronous optical and electrical detection of biomolecules traversing through solid-state nanopores. Rev Sci Instrum. Jan. 2010;81(1):014301. doi: 10.1063/1.3277116.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Stoltenburg et al., SELEX—a (r)evolutionary method to generate high-affinity nucleic acid ligands. Biomol Eng. Oct. 2007;24(4):381-403. Epub Jun. 16, 2007.
Tazi et al., Alternative splicing and disease. Biochim Biophys Acta. Jan. 2009;1792(1):14-26. doi: 10.1016/j.bbadis.2008.09.017. Epub Oct. 17, 2008.
Tian et al., Designing a polycationic probe for simultaneous enrichment and detection of microRNAs in a nanopore. ACS Nano. May 28, 2013;7(5):3962-9. doi: 10.1021/nn305789z. Epub Apr. 10, 2013.

Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tuerk et al., Systematic evolution of ligands by exponential enrichment: RNA ligands to bacteriophage T4 DNA polymerase. Science. Aug. 3, 1990;249(4968):505-10.
Van Heel et al., Single-particle electron cryo-microscopy:towards atomic resolution. Q Rev Biophys. Nov. 2000;33(4):307-69.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Wang et al., Nanopore-based detection of circulating microRNAs in lung cancer patients. Nat Nanotechnol. Sep. 4, 2011;6(10):668-74. doi: 10.1038/nnano.2011.147.
Wang et al., Serum miR-146a and miR-223 as potential new biomarkers for sepsis. Biochem Biophys Res Commun. Mar. 26, 2010;394(1):184-8. doi: 10.1016/j.bbrc.2010.02.145. Epub Feb. 24, 2010.
Wanunu et al., Rapid electronic detection of probe-specific microRNAs using thin nanopore sensors. Nat Nanotechnol. Nov. 2010;5(11):807-14. doi: 10.1038/nnano.2010.202. Epub Oct. 24, 2010.
White et al., Generation of species cross-reactive aptamers using "toggle" SELEX. Mol Ther. Dec. 2001;4(6):567-73.
Wightman et al., Posttranscriptional regulation of the heterochronic gene lin-14 by lin-4 mediates temporal pattern formation in C. elegans. Cell. Dec. 3, 1993;75(5):855-62.
Yoshina-Ishii et al., Arrays of mobile tethered vesicles on supported lipid bilayers. J Am Chem Soc. Apr. 2, 2003;125(13):3696-7.
Case 1:17-cv-01353-LPS Document 15. Plaintiff's response to Oxford Nanopore Techologies, Inc.'s Motion to Dismiss and Request for Scheduling Conference. Nov. 30, 2017.
Case 1:17-cv-01353-LPS Document 13. First Amended Complaint for Patent Infringement. Nov. 30, 2017.
Case 1:17-cv-01353-RGA Document 10. Oxford's opening brief in support of its motion to partially dismiss Pacbio's complaint for patent infringement. Nov. 16, 2017.
United States District Court for the District of Delaware Order. *Pacific Biosciences of California, Inc.* v. *Oxford Nanopore Technolgoies, Inc.* Civil Action No. 17-275-RGA. Nov. 9, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-LPS Document 18. Notice of subsequent events relating to Oxford's motion to dismiss (D.I. 9). Oct. 18, 2017.
Case 1:17-cv-00275-RGA Document 16. Oxford's reply brief in support of its motion to dismiss PacBio's complaint for patent infringement. Jun. 26, 2017.
Case 1:17-cv-00275-RGA Document 14. PacBio's response to Oxford's motion to dismiss. Jun. 5, 2017.
Case 1:17-cv-00275-RGA Document 10. Oxford's opening brief in support of its motion to dismiss PacBio's complaint for patent infringement. May 8, 2017.
Kozarewa et al., 96-plea molecular barcoding for the Illumina Genome Analyzer. Methods Mol Biol. 2011;733:279-298. doi:10.1007/978-1-61779-089-8_20.
Chen et al., A cost-effective method for Illumina small RNA-Seq library preparation using T4 RNA ligase 1 adenylated adapters. Plant Methods. 2012;8(1):41. Published Sep. 20, 2012. doi:10.1186/1746-4811-8-41.
Van Nieuwerburgh et al., Quantitative bias in Illumina TruSeq and a novel post amplification barcoding strategy for multiplexed DNA and small RNA deep sequencing. PLoS One. 2011;6(10):e26969. doi:10.1371/journal.pone.0026969.

\* cited by examiner

A

B

C

D

METHOD OF CHARACTERIZING A TARGET RIBONUCLEIC ACID (RNA) COMPRISING FORMING A COMPLEMENTARY POLYNUCLEOTIDE WHICH MOVES THROUGH A TRANSMEMBRANE PORE

This application is a national stage filing under U.S.C. § 371 of PCT International Application PCT/GB2014/053121, with an international filing date of Oct. 17, 2014, which claims foreign priority benefits under 35 U.S.C. § 119(a)-(d) or 35 U.S.C. § 365(b) of British application number 1318465.0, filed Oct. 18, 2013, which are herein incorporated by reference in their entirety.

FIELD OF THE INVENTION

The invention relates to a new method of characterising a target ribonucleic acid (RNA) involving forming a complementary polynucleotide. The method uses a transmembrane pore.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the "strand sequencing method, a single polynucleotide strand is passed through the pore and the identity of the nucleotides are derived. Strand sequencing can involve the use of a nucleotide handling protein, such as a helicase, to control the movement of the polynucleotide through the pore.

One group of RNAs which are difficult to detect in low concentrations are micro-ribonucleic acids (micro-RNA or miRNAs). miRNAs are highly stable RNA oligomers, which can regulate protein production post-transcriptionally. They act by one of two mechanisms. In plants, miRNAs have been shown to act chiefly by directing the cleavage of messenger RNA, whereas in animals, gene regulation by miRNAs typically involves hybridisation of miRNAs to the 3' UTRs of messenger RNAs, which hinders translation (Lee et al., Cell 75, 843-54 (1993); Wightman et al., Cell 75, 855-62 (1993); and Esquela-Kerscher et al., Cancer 6, 259-69 (2006)). miRNAs frequently bind to their targets with imperfect complementarity. They have been predicted to bind to as many as 200 gene targets each and to regulate more than a third of all human genes (Lewis et al., Cell 120, 15-20 (2005)).

The expression level of certain microRNAs is known to change in tumours, giving different tumour types characteristic patterns of microRNA expression (Rosenfeld, N. et al., Nature Biotechnology 26, 462-9 (2008)). In addition, miRNA profiles have been shown to be able to reveal the stage of tumour development with greater accuracy than messenger RNA profiles (Lu et al., Nature 435, 834-8 (2005) and Barshack et al., The International Journal of Biochemistry & Cell Biology 42, 1355-62 (2010)). These findings, together with the high stability of miRNAs, and the ability to detect circulating miRNAs in serum and plasma (Wang et al., Biochemical and Biophysical Research Communications 394, 184-8 (2010); Gilad et al., PloS One 3, e3148 (2008); and Keller et al., Nature Methods 8, 841-3 (2011)), have led to a considerable amount of interest in the potential use of microRNAs as cancer biomarkers. For treatment to be effective, cancers need to be classified accurately and treated differently, but the efficacy of tumour morphology evaluation as a means of classification is compromised by the fact that many different types of cancer share morphological features. miRNAs offer a potentially more reliable and less invasive solution.

SUMMARY OF THE INVENTION

The inventors have surprisingly demonstrated that it is possible to characterise a target RNA by forming a complementary polynucleotide from the target RNA and then characterising the complementary polynucleotide using a transmembrane pore. The invention therefore provides a method of characterising a target RNA, comprising:

(a) forming a complementary polynucleotide from the target RNA;

(b) contacting the complementary polynucleotide with a transmembrane pore such that the complementary polynucleotide moves through the pore; and (c) taking one or more measurements as the complementary polynucleotide moves with respect to the pore wherein the measurements are indicative of one or more characteristics of the complementary polynucleotide and thereby characterising the target RNA.

The invention also provides:

a method of determining whether or not a patient has or is at risk of developing a disease or condition associated with an altered amount and/or alternate splicing of messenger RNA (mRNA), comprising determining the amount and/or identity of the mRNA in a sample from the patient using a method of the invention and thereby determining whether or not the patient has or is at risk of developing the disease or condition;

a method of determining whether or not a patient has or is at risk of developing a disease or condition associated with a miRNA, comprising determining the presence or absence of the miRNA in a sample from the patient using a method of the invention and thereby determining whether or not a patient has or is at risk of developing the disease or condition;

a kit for characterising a target RNA comprising (a) a transmembrane pore and (b) a reverse transcriptase enzyme and/or a reverse transcription primer; and an apparatus for characterising target RNAs in a sample, comprising (a) a plurality of transmembrane pores and (b) a plurality of reverse transcriptase enzymes and/or a plurality of reverse transcription primers.

DESCRIPTION OF THE SEQUENCE LISTING

Figure 1:
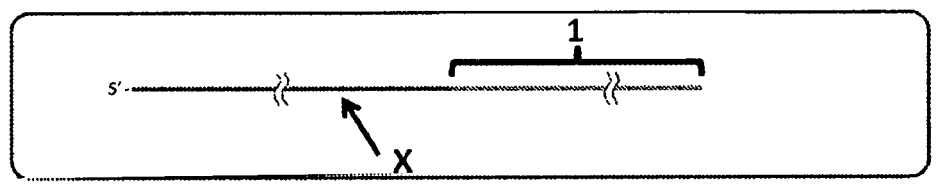
FIG. 1 shows the sample preparation procedure outlined in Example 1 and 2. A sample of mRNA (shown in step A, labelled X) is annealed to a capture strand (shown in step B, labelled Y). The capture strand anneals to the mRNA at the polyA region (labelled 1, this region can vary in length depending on the mRNA). A reverse transcriptase enzyme forms the complementary cDNA strand (shown in step C as a dotted line) to the mRNA. The tether (shown in step D, labelled Z) then anneals to the cDNA.
Figure 1:
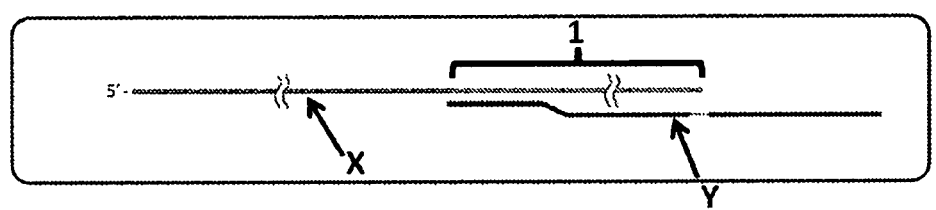
Figure 1:
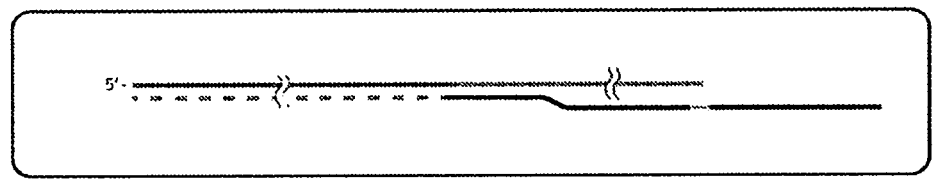
Figure 1:
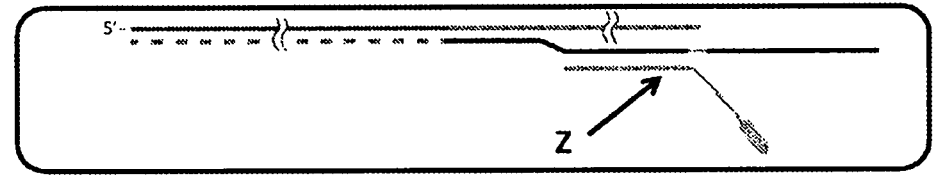

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence of the messenger RNA used in Examples 1 and 2.

SEQ ID NO: 9 shows part of the polynucleotide sequence which makes up the primer used in Example 1. The 3' end of SEQ ID NO: 9 is attached by four iSpC3 spacers to the 5' end of SEQ ID NO: 10.

SEQ ID NO: 10 shows part of the polynucleotide sequence which makes up the primer used in Example 1. The 5' end of SEQ ID NO: 10 is attached by four iSpC3 spacers to the 3' end of SEQ ID NO: 9.

SEQ ID NO: 11 shows the polynucleotide sequence of the cDNA transcribed from SEQ ID NO: 8 which is attached at its 5' end to the 3' end of the primer sequence (SEQ ID NO: 10 which is attached by four iSpC3 spacers to the 3' end of SEQ ID NO: 9).

SEQ ID NO: 12 shows the polynucleotide sequence of the strand used to tether the cDNA/mRNA in Examples 2 and 3. Attached to the 3' end of SEQ ID NO: 11 is six iSp18 spacers which are attached to two thymine residues and a 3' cholesterol TEG.

SEQ ID NO: 13 shows the amino acid sequence of T4 Dda helicase.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a target RNA" includes two or more target RNAs, reference to "a complementary polynucleotide" includes two or more such complementary polynucleotides, reference to "a transmembrane protein pore" includes two or more such pores, and the like.

All publications, patents and patent applications cited herein, whether supra or infra, are hereby incorporated by reference in their entirety.

Characterising a Target RNA

The invention provides a method of characterising a target ribonucleic acid (RNA). A complementary polynucleotide is formed from the target RNA and the complementary polynucleotide is characterised using a transmembrane pore. This allows characterisation of the target RNA. The target RNA is preferably not ligated to a non-RNA leader, such as a DNA leader.

The method of the invention, and in particular the sample preparation involved, is straightforward and simple. Since the transmembrane pore is capable of detecting single molecule of the complementary polynucleotide, there is no need for amplification of the target RNA or complementary polynucleotide. The method typically does not comprise polymerase chain reaction (PCR) or reverse transcription PCR (RT-PCR). This considerably reduces the amount of workflow needed to characterise a target RNA. It also avoids any biases and artifacts introduced by PCR.

Target RNA

RNA is a macromolecule comprising two or more ribonucleotides. The target RNA may comprise any combination of any ribonucleotides. The ribonucleotides can be naturally occurring or artificial. One or more ribonucleotides in the target RNA can be oxidized or methylated. One or more ribonucleotides in the target RNA may be damaged. For instance, the target RNA may comprise a pyrimidine dimer, such as a uracil dimer. Such dimers are typically associated with damage by ultraviolet light and are the primary cause of skin melanomas. One or more ribonucleotides in the target RNA may be modified, for instance with a label or a tag. Suitable labels are described below. The target RNA may comprise one or more spacers.

A ribonucleotide typically contains a nucleobase, a ribose sugar and at least one phosphate group. The nucleobase is typically heterocyclic. Nucleobases include, but are not limited to, purines and pyrimidines and more specifically adenine, guanine, thymine, uracil and cytosine. The nucleotide typically contains a monophosphate, diphosphate or triphosphate. Phosphates may be attached on the 5' or 3' side of a nucleotide.

Ribonucleotides include, but are not limited to, adenosine monophosphate (AMP), guanosine monophosphate (GMP), thymidine monophosphate (TMP), uridine monophosphate (UMP), cytidine monophosphate (CMP), 5-methylcytidine monophosphate, 5-methylcytidine diphosphate, 5-methylcytidine triphosphate, 5-hydroxymethylcytidine monophosphate, 5-hydroxymethylcytidine diphosphate and 5-hydroxymethylcytidine triphosphate. The nucleotides are preferably selected from AMP, TMP, GMP, CMP and UMP.

A ribonucleotide may be abasic (i.e. lack a nucleobase). A ribonucleotide may also lack a nucleobase and a sugar (i.e. is a C3 spacer).

The ribonucleotides in the target RNA may be attached to each other in any manner. The ribonucleotides are typically attached by their sugar and phosphate groups as in nucleic acids. The ribonucleotides may be connected via their nucleobases as in pyrimidine dimers.

The target RNA may be single stranded or double stranded.

The target RNA is preferably messenger RNA (mRNA). The target mRNA may be an alternate splice variant. Altered amounts (or levels) of mRNA and/or alternate mRNA splice variants may be associated with diseases or conditions.

The target RNA is preferably a microRNA (or miRNA). Suitable miRNAs for use in the invention are well known in the art. For instance, suitable miRNAs are stored on publically available databases (Jiang Q., Wang Y., Hao Y., Juan L., Teng M., Zhang X., Li M., Wang G., Liu Y., (2009) miR2 Disease: a manually curated database for microRNA deregulation in human disease. Nucleic Acids Res.). The use of mRNAs and miRNAs to diagnose or prognose diseases or conditions are discussed in more detail below.

The whole or only part of the target RNA may be characterised using this method. The target RNA can be any length. For example, the RNA can be at least 10, at least 50, at least 100, at least 150, at least 200, at least 250, at least 300, at least 400 or at least 500 ribonucleotides in length. The target RNA can be 1000 or more ribonucleotides, 5000 or more ribonucleotides in length or 100000 or more ribonucleotides in length.

The target RNA is typically present in or derived from any suitable sample. The invention is typically carried out on a sample that is known to contain or suspected to contain the target RNA. Alternatively, the invention may be carried out on a sample to confirm the identity of one or more target RNAs whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The target RNA is preferably eukaryotic. For instance, the target RNA may be derived from a eukaryotic cell or may be derived from a virus using a eukaryotic cell's transcription machinery. The invention may be carried out in vitro on a sample obtained from or extracted from any virus.

The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa or cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C. The target RNA is typically extracted from the sample before it is used in the method of the invention. RNA extraction kits are commercially available from, for instance, New England Biolabs® and Invitrogen®.

No Amplification

The target RNA is typically not amplified in the method of the invention. The method typically does not comprise making multiple copies of the target RNA.

The complementary polynucleotide is typically not amplified in the method of the invention. The method typically does not comprise making multiple copies of the complementary polynucleotide.

The method preferably does not comprise polymerase chain reaction (PCR) or reverse transcription PCR (RT-PCR).

Step (a)

The method of the invention comprises forming a complementary polynucleotide from the target RNA. The polynucleotide may be complementary to part of or all of the target RNA. If the polynucleotide is complementary to part of the target RNA, it is typically complementary to a sufficient amount of the target RNA that it may be characterised in accordance with the invention.

The polynucleotide is typically complementary based on the pairing of its nucleobases, typically adenine (A), guanine (G), thymine (T) and cytosine (C), with their RNA base counterparts, typically uracil (U), cytosine (C), adenine (A) and guanine (G) respectively.

A polynucleotide, such as a nucleic acid, is a macromolecule comprising two or more nucleotides. The polynucleotide or nucleic acid may comprise any combination of any nucleotides. At least a portion of the polynucleotide is complementary to all of or part of the target RNA. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide in the polynucleotide is typically a ribonucleotide or deoxyribonucleotide. The nucleotide is preferably a deoxyribonucleotide. The nucleotide typically contains a monophosphate, diphosphate or triphosphate. Phosphates may be attached on the 5' or 3' side of a nucleotide.

Nucleotides for use in the polynucleotides of the invention include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP. The nucleotides are most preferably selected from dAMP, dTMP, dGMP, dCMP and dUMP. The polynucleotide preferably comprises the following nucleotides: dAMP, dUMP and/or dTMP, dGMP and dCMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide is typically single stranded. The polynucleotide can be a nucleic acid, such as deoxyribonucleic acid (DNA) or ribonucleic acid (RNA). The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The complementary polynucleotide is most preferably complementary deoxyribonucleic acid (cDNA).

The complementary polynucleotide may be any length. The complementary polynucleotide is typically the same length as the target RNA. For example, the complementary polynucleotide can be at least 10, at least 50, at least 100, at least 150, at least 200, at least 250, at least 300, at least 400 or at least 500 deoxyribonucleotides in length. The complementary polynucleotide can be 1000 or more deoxyribonucleotides, 5000 or more deoxyribonucleotides in length or 100000 or more deoxyribonucleotides in length.

The complementary polynucleotide may be formed from the target RNA using any known method. Enzymes which convert RNA to complementary nucleic acids such as those described above are known in the art.

If the complementary polynucleotide is cDNA, the method comprises reverse transcribing the target RNA to form a cDNA. Step (a) preferably comprising reverse transcribing the target RNA using a reverse transcriptase to form the cDNA. The reverse transcriptase may reverse transcribe all or part of the available target RNA. Reverse transcriptases are enzymes which are capable of catalysing the formation of cDNA from a RNA template. They are commercially available from, for instance, New England Biolabs® and Invitrogen®. The target RNA is typically contacted with the reverse transcriptase in the presence of a population of deoxyribonucleotides as defined above. The population typically comprises all of the deoxyribonucleotides needed to base pair with each of the ribonucleotides in the target RNA. The population of deoxyribonucleotides typically comprises dAMP, dTMP, dGMP and dCMP.

Primers

Step (a) preferably comprises hybridising a primer to the target RNA and using the primer to form the complementary polynucleotide. The primer typically assists with conversion of the target RNA to the complementary polynucleotide. For instance, the double stranded region formed by hybridisation of the primer to the target RNA may provide a binding site for a reverse transcriptase. The reverse transcriptase may then reverse transcribe the remainder of the target RNA to form cDNA. The complementary polynucleotide, such as cDNA, produced in step (a) is typically attached to the primer. The primer may comprise a bridging moiety, such as a hairpin loop, as discussed below.

Using a primer has various advantages. It avoids the need to amplify the target RNA using PCR. This reduces the amount of workflow that needs to be carried out and avoids any biases and artifacts introduced by PCR. Since the primer can be designed to bind at a specific end of the target RNA (see below), the complementary polynucleotide can be formed in a specific direction and the complementary polynucleotide can be moved through the pore is a known direction. This facilitates the characterisation of the target RNA.

The primer is typically a polynucleotide. The polynucleotide may be any of those discussed above.

The primer preferably comprises a leader sequence and/or a region to which a polynucleotide binding protein is capable of binding. The leader sequence facilitates the method of the invention. The leader sequence is designed to preferentially thread into the transmembrane pore and thereby facilitate the movement of the complementary polynucleotide through the pore. The leader sequence is typically a polynucleotide, such as DNA or RNA, a modified polynucleotide (such as abasic DNA), PNA, LNA, PEG or a polypeptide. The leader is preferably a polynucleotide and is more preferably a single stranded polynucleotide. The leader sequence can be any of the polynucleotides discussed above. The single stranded leader sequence is most preferably a single strand of DNA. The leader sequence can be any length, but is typically 27 to 150 nucleotides in length, such as from 50 to 150 nucleotides in length.

The region to which a polynucleotide binding protein is capable of binding is typically a polynucleotide. It can be any of the polynucleotides discussed above. The region may correspond to the leader sequence. Alternatively, the region may be distinct from the leader sequence. The polynucleotide binding protein may help to control the movement of the complementary polynucleotide through the pore as discussed in more detail below.

As discussed above, the target RNA is preferably eukaryotic. Eukaryotic RNA typically comprises polyA tail, i.e. a stretch of consecutive adenosine monophosphates. The polyA tail is typically at the 3' end of the RNA. In such embodiments, step (a) preferably comprises hybridising a primer to the polyA tail of the target RNA and using the primer to reverse transcribe the target RNA to form the complementary polynucleotide. The primer preferably comprises a polyT region, i.e. region containing only nucleotides based on thymine. The polyT region may contain TMP or dTMP. The polyT region may be any length, such as at least 10, at least 15, at least 20, at least 25 or more. The primer is preferably a polyT-VN primer, which comprises a polyT region and a VN anchor where V is dAMP, dCMP or dGMP and N is dAMP, dCMP, dGMP or dTMP. Such primers are commercially available, such as from New England Biolabs®.

For non-eukaryotic target RNA, such as bacterial target RNA, step (a) further comprises adding a polyA tail to the target RNA, for instance using a polyA polymerase and ATP. Step (a) may further comprise hybridising a primer to the added polyA tail as described above.

Steps (b) and (c)

The method of the invention also comprises (b) contacting the complementary polynucleotide with a transmembrane pore. The method also comprises (c) taking one or more measurements as the complementary polynucleotide moves with respect to the pore wherein the measurements are indicative of one or more characteristics of the complementary polynucleotide and thereby characterising the target RNA.

Steps (b) and (c) are preferably carried out with a potential applied across the pore. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5. In some instances, the current passing through the pore as the polynucleotide moves with respect to the pore is used to determine the sequence of the complementary polynucleotide and hence the sequence of the target RNA. This is Strand Sequencing.

The complementary polynucleotide may be contacted with the pore when it is fully or partially hybridized to the target RNA. Alternatively, the complementary polynucleotide may be contacted with the pore in the absence of the target RNA. In such embodiments, step (a) preferably further comprises removing the target RNA, for instance by digesting the target RNA. Step (a) may further comprise contacting the target RNA with RNAse H. This enzyme specifically digests the RNA strand of RNA:DNA duplexes.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro. The complementary polynucleotide is preferably coupled to the membrane. This may be done using any known method. The complementary polynucleotide is preferably coupled to the membrane comprising the transmembrane pore. The method may comprise coupling the complementary polynucleotide to the membrane comprising the transmembrane pore. The polynucleotide is preferably coupled to the membrane using one or more anchors. The polynucleotide may be coupled to the membrane using any known method.

Each anchor comprises a group which couples (or binds) to the polynucleotide and a group which couples (or binds) to the membrane. Each anchor may covalently couple (or bind) to the polynucleotide and/or the membrane. If a Y adaptor and/or a hairpin loop adaptors are used, the polynucleotide is preferably coupled to the membrane using the adaptor(s).

The polynucleotide may be coupled to the membrane using any number of anchors, such as 2, 3, 4 or more anchors. For instance, a polynucleotide may be coupled to the membrane using two anchors each of which separately couples (or binds) to both the polynucleotide and membrane.

The one or more anchors may comprise the one or more helicases and/or the one or more molecular brakes discussed below.

If the membrane is an amphiphilic layer, such as a lipid bilayer (as discussed in detail above), the complementary polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The complementary polynucleotide may be coupled directly to the membrane. It may be coupled to the membrane using any of the ways disclosed in International Application Number No. PCT/GB2012/051191 (published as WO 2012/164270). The complementary polynucleotide is preferably coupled to the membrane via a linker. Preferred linkers include, but are not limited to, polymers, such as polynucleotides, polyethylene glycols (PEGs) and polypeptides. If a complementary polynucleotide is coupled directly to the membrane, then some data will be lost as the characterising run cannot continue to the end of the complementary polynucleotide due to the distance between the membrane and the pore and/or polynucleotide binding protein. If a linker is used, then the complementary polynucleotide can be processed to completion. If a linker is used, the linker may be attached to the complementary polynucleotide at any position. The linker is typically attached to the complementary polynucleotide at the tail polymer.

The coupling may be stable or transient. For certain applications, the transient nature of the coupling is preferred. If a stable coupling molecule were attached directly to either the 5' or 3' end of a complementary polynucleotide, then some data will be lost as the characterising run cannot continue to the end of the complementary polynucleotide due to the distance between the membrane and the pore and/or polynucleotide binding protein. If the coupling is transient, then when the coupled end randomly becomes free of the membrane, then the complementary polynucleotide can be processed to completion. Chemical groups that form stable or transient links with the membrane are discussed in more detail below. The complementary polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the complementary polynucleotide is coupled to an amphiphilic layer. Coupling of polynucleotides to synthetic lipid bilayers has been carried out previously with various different tethering strategies. These are summarised in Table 1 below.

TABLE 1

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V, R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Complementary polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for complementary polynucleotides. Each different modification group tethers the complementary polynucleotide in a slightly different way and coupling is not always permanent so giving different dwell times for the complementary polynucleotide to the membrane. The advantages of transient coupling are discussed above.

Coupling of complementary polynucleotides can also be achieved by a number of other means provided that a reactive group can be added to the complementary polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be a short region in the polynucleotide complementary to one already coupled to the membrane, so that attachment can be achieved via hybridisation. The region could be part of the complementary polynucleotide or ligated to it. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). The coupling chemistry can be incorporated during the formation of the complementary polynucleotide from the target RNA. For instance, the complementary polynucleotide can be synthesized using a primer with a reactive group attached to it.

Most preferably, the complementary polynucleotide is coupled to the membrane using a cholesterol-tagged polynucleotide which hybridises to the complementary polynucleotide or primer attached thereto.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide or nucleic acid, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-(B1)8 and is called MS-(B2)8. The pore used in the invention is preferably MS-(B2)8. The further preferred variant comprises the mutations G75S/G77S/L88N/Q126R. The variant of SEQ ID NO: 2 has the mutations G75S/G77S/L88N/Q126R in addition to all the mutations of MS-(B1)8 and is called MS-(B2C)8 The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| | | | | |
|---|---|---|---|---|
| Ala | aliphatic, hydrophobic, neutral | | Met | hydrophobic, neutral |
| Cys | polar, hydrophobic, neutral | | Asn | polar, hydrophilic, neutral |
| Asp | polar, hydrophilic, charged (−) | | Pro | hydrophobic, neutral |
| Glu | polar, hydrophilic, charged (−) | | Gln | polar, hydrophilic, neutral |
| Phe | aromatic, hydrophobic, neutral | | Arg | polar, hydrophilic, charged (+) |
| Gly | aliphatic, neutral | | Ser | polar, hydrophilic, neutral |
| His | aromatic, polar, hydrophilic, charged (+) | | Thr | polar, hydrophilic, neutral |
| Ile | aliphatic, hydrophobic, neutral | | Val | aliphatic, hydrophobic, neutral |
| Lys | polar, hydrophilic, charged(+) | | Trp | aromatic, hydrophobic, neutral |
| Leu | aliphatic, hydrophobic, neutral | | Tyr | aromatic, polar, hydrophobic |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described below.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the helicase or construct. The variant preferably comprises one or more reactive cysteine residues that facilitate attachment to the helicase or construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive S⁻ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Step (b) preferably comprises contacting the complementary polynucleotide with a polynucleotide binding protein such that the protein controls the movement of the complementary polynucleotide through the pore. Any polynucleotide binding protein may be used. The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target sequence and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31.

Preferred enzymes are polymerases, exonucleases, helicases and topoisomerases, such as gyrases. The enzyme may be any of those disclosed in International Application No. PCT/GB10/000133 (published as WO 2010/086603). The helicase may a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925; PCT/GB2013/051924; PCT/GB2013/051928; and the UK Application being filed concurrently with this application (ONT IP 049).

In one embodiment, the method involves contacting the complementary polynucleotide with a helicase such that the helicase controls the movement of the complementary polynucleotide through the pore. Any helicase may be used in the method. Helicases may work in two modes with respect to the pore. First, the method is preferably carried out using a helicase such that it controls movement of the polynucleotide through the pore with the field resulting from the applied voltage. In this mode the 5' end of the polynucleotide is first captured in the pore, and the enzyme controls movement of the polynucleotide into the pore such that the polynucleotide is passed through the pore with the field until it finally translocates through to the trans side of the bilayer. Alternatively, the method is preferably carried out such that a helicase enzyme controls movement of the polynucleotide through the pore against the field resulting from the applied voltage. In this mode the 3' end of the polynucleotide is first captured in the pore, and the enzyme controls movement of the polynucleotide through the pore such that the polynucleotide is pulled out of the pore against the applied field until finally ejected back to the cis side of the bilayer.

The polynucleotide binding protein may be covalently attached to the pore. The polynucleotide binding protein is preferably not covalently attached to the pore. The application of a voltage to the pore and helicase or construct may result in the formation of a sensor that is capable of characterising the complementary polynucleotide. This is discussed in more detail below.

Any of the proteins described herein may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the helicase, pore or construct. An example of this would be to react a gel-shift reagent to a cysteine engineered on the outside of the pore. This has been demonstrated as a method for separating hemolysin hetero-oligomers (Chem Biol. 1997 July; 4 (7):497-505).

The target RNA, complementary polynucleotide, polynucleotide binding protein or pore may be labelled with a revealing label. The revealing label may be any suitable label which can be detected. Suitable labels include, but are not limited to, fluorescent molecules, radioisotopes, e.g. $^{125}$I, $^{35}$S, enzymes, antibodies, antigens, polynucleotides and ligands such as biotin.

Proteins may be made synthetically or by recombinant means. For example, proteins may be synthesized by in vitro translation and transcription (IVTT). The amino acid sequence of the protein may be modified to include non-naturally occurring amino acids or to increase the stability of the protein. When a protein is produced by synthetic means, such amino acids may be introduced during production. Proteins may also be altered following either synthetic or recombinant production.

Proteins may also be produced using D-amino acids. For instance, the pore or polynucleotide binding protein may comprise a mixture of L-amino acids and D-amino acids. This is conventional in the art for producing such proteins or peptides.

The proteins used in the invention may also contain other non-specific modifications as long as they do not interfere with the proteins' function. A number of non-specific side chain modifications are known in the art and may be made to the side chains of the protein(s). Such modifications include, for example, reductive alkylation of amino acids by reaction with an aldehyde followed by reduction with NaBH$_4$, amidination with methylacetimidate or acylation with acetic anhydride.

Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The gene encoding the sequence of interest may be amplified using PCR involving specific primers. The amplified sequences may then be incorporated into a recombinant replicable vector such as a cloning vector. The vector may be used to replicate the polynucleotide in a compatible host cell. Thus polynucleotide sequences may be made by introducing a polynucleotide encoding the sequence of interest into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or $\lambda_L$ promoter is typically used.

The host cell typically expresses the construct at a high level. Host cells transformed with a polynucleotide sequence will be chosen to be compatible with the expression vector used to transform the cell. The host cell is typically bacterial and preferably E. coli. Any cell with a λ DE3 lysogen, for example Rosetta2(DE3)pLys, C41 (DE3), BL21 (DE3), JM109 (DE3), B834 (DE3), TUNER, Origami and Origami B, can express a vector comprising the T7 promoter.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target RNA. The method may involve measuring two, three, four or five or more characteristics of the target RNA. The one or more characteristics are preferably selected from (i) the length of the target RNA, (ii) the identity of the target RNA, (iii) the sequence of the target RNA, and (iv) the amount of the target RNA. Any combination of (i) to (iv) may be measured in accordance with the invention.

For (i), the length of the RNA may be measured for example by forming a complementary polynucleotide of the same length and determining the number of interactions between the complementary polynucleotide and the pore or the duration of interaction between the complementary polynucleotide and the pore.

For (ii), the identity of the RNA may be measured in a number of ways. The identity of the RNA may be measured in conjunction with measurement of the sequence of the complementary polynucleotide or without measurement of the sequence of the complementary polynucleotide. The former is straightforward; the complementary polynucleotide is sequenced and the sequence of the target RNA is thereby identified (since it is complementary). The latter may be done in several ways. For instance, the presence of a particular motif in the complementary polynucleotide may be measured (without measuring the remaining sequence of the polynucleotide). Alternatively, the measurement of a particular electrical and/or optical signal in the method may identify the complementary polynucleotide and thereby identify the target RNA.

For (iii), the sequence of the complementary polynucleotide and hence the sequence of the target RNA can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the amount of the target RNA may be measured in a variety of ways. For instance, since the target RNA is typically not amplified in the method of the invention, the amount of the target RNA may be measured by counting the number of complementary polynucleotides which interact with the transmembrane pore. The number of complementary polynucleotides (i.e. the number of instances of the complementary polynucleotide) typically corresponds to the number of the target RNA molecules (i.e. the number of instances of the target RNA).

A variety of different types of measurements may be made. This includes without limitation: electrical measurements and optical measurements. Possible electrical measurements include: current measurements, impedance measurements, tunneling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1): 014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:

(a) contacting the complementary polynucleotide with a transmembrane pore and a polynucleotide binding protein such that the protein controls the movement of the polynucleotide through the pore; and (b) measuring the current passing through the pore as the polynucleotide moves with respect to the pore wherein the current is indicative of one or more characteristics of the complementary polynucleotide and thereby characterising the target RNA.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Examples. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. Hel308, XPD, RecD and TraI helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method may be carried out in the presence of free nucleotides or free nucleotide analogues and/or an enzyme cofactor that facilitates the action of the helicase or construct. The method may also be carried out in the absence of free nucleotides or free nucleotide analogues and in the absence of an enzyme cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase or construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Helicase(s) and Molecular Brake(s)

In a preferred embodiment, the method comprises:
 (a) providing the complementary polynucleotide with one or more helicases and one or more molecular brakes attached to the polynucleotide;
 (b) contacting the complementary polynucleotide with a transmembrane pore and applying a potential across the pore such that the one or more helicases and the one or more molecular brakes are brought together and both control the movement of the polynucleotide through the pore;
 (c) taking one or more measurements as the complementary polynucleotide moves with respect to the pore wherein the measurements are indicative of one or more characteristics of the polynucleotide and thereby characterising the polynucleotide.

This type of method is discussed in detail in the International application PCT/GB2014/052737.

The one or more helicases may be any of those discussed above. The one or more molecular brakes may be any compound or molecule which binds to the polynucleotide and slows the movement of the polynucleotide through the pore. The one or more molecular brakes preferably comprise one or more compounds which bind to the polynucleotide.

The one or more compounds are preferably one or more macrocycles. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) J Am. Chem. Soc. 116, 6081-6088. The agent is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD).

The one or more molecular brakes are preferably not one or more single stranded binding proteins (SSB). The one or more molecular brakes are more preferably not a single-stranded binding protein (SSB) comprising a carboxy-terminal (C-terminal) region which does not have a net negative charge or (ii) a modified SSB comprising one or more modifications in its C-terminal region which decreases the net negative charge of the C-terminal region. The one or more molecular brakes are most preferably not any of the SSBs disclosed in International Application No. PCT/GB2013/051924 (published as WO 2014/013259).

The one or more molecular brakes are preferably one or more polynucleotide binding proteins. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. The one or more molecular brakes may be derived from any of the polynucleotide handling enzymes discussed above. Modified versions of Phi29 polymerase (SEQ ID NO: 8) which act as molecular brakes are disclosed in U.S. Pat. No. 5,576,204. The one or more molecular brakes are preferably derived from a helicase.

Any number of molecular brakes derived from a helicase may be used. For instance, 1, 2, 3, 4, 5, 6, 7, 8, 9, 10 or more helicases may be used as molecular brakes. If two or more helicases are be used as molecular brakes, the two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. The one or more molecular brakes derived from helicases are preferably modified to reduce the size of an opening in the polynucleotide binding domain through which in at least one conformational state the polynucleotide can unbind from the helicase. This is disclosed in WO 2014/013260.

Preferred helicase constructs for use in the invention are described in International Application Nos. PCT/GB2013/051925 (published as WO 2014/013260); PCT/GB2013/

051924 (published as WO 2014/013259) PCT/GB2013/051928 (published as WO 2014/013262) and PCT/GB2014/052736.

If the one or more helicases are used in the active mode (i.e. when the one or more helicases are provided with all the necessary components to facilitate movement, e.g. ATP and $Mg^{2+}$), the one or more molecular brakes are preferably (a) used in an inactive mode (i.e. are used in the absence of the necessary components to facilitate movement or are incapable of active movement), (b) used in an active mode where the one or more molecular brakes move in the opposite direction to the one or more helicases or (c) used in an active mode where the one or more molecular brakes move in the same direction as the one or more helicases and more slowly than the one or more helicases.

If the one or more helicases are used in the inactive mode (i.e. when the one or more helicases are not provided with all the necessary components to facilitate movement, e.g. ATP and $Mg^{2+}$ or are incapable of active movement), the one or more molecular brakes are preferably (a) used in an inactive mode (i.e. are used in the absence of the necessary components to facilitate movement or are incapable of active movement) or (b) used in an active mode where the one or more molecular brakes move along the polynucleotide in the same direction as the polynucleotide through the pore.

The one or more helicases and one or more molecular brakes may be attached to the polynucleotide at any positions so that they are brought together and both control the movement of the polynucleotide through the pore. The one or more helicases and one or more molecular brakes are at least one nucleotide apart, such as at least 5, at least 10, at least 50, at least 100, at least 500, at least 1000, at least 5000, at least 10,000, at least 50,000 nucleotides or more apart. If the method concerns characterising a double stranded polynucleotide provided with a Y adaptor at one end and a hairpin loop adaptor at the other end, the one or more helicases are preferably attached to the Y adaptor and the one or more molecular brakes are preferably attached to the hairpin loop adaptor. In this embodiment, the one or more molecular brakes are preferably one or more helicases that are modified such that they bind the polynucleotide but do not function as a helicase. The one or more helicases attached to the Y adaptor are preferably stalled at a spacer as discussed in more detail below. The one or more molecular brakes attach to the hairpin loop adaptor are preferably not stalled at a spacer. The one or more helicases and the one or more molecular brakes are preferably brought together when the one or more helicases reach the hairpin loop. The one or more helicases may be attached to the Y adaptor before the Y adaptor is attached to the polynucleotide or after the Y adaptor is attached to the polynucleotide. The one or more molecular brakes may be attached to the hairpin loop adaptor before the hairpin loop adaptor is attached to the polynucleotide or after the hairpin loop adaptor is attached to the polynucleotide.

The one or more helicases and the one or more molecular brakes are preferably not attached to one another. The one or more helicases and the one or more molecular brakes are more preferably not covalently attached to one another. The one or more helicases and the one or more molecular brakes are preferably not attached as described in International Application Nos. PCT/GB2013/051925 (published as WO 2014/013260); PCT/GB2013/051924 (published as WO 2014/013259) PCT/GB2013/051928 (published as WO 2014/013262) and PCT/GB2014/052736.

Spacers

The one or more helicases may be stalled at one or more spacers as discussed in International Application No. PCT/GB2014/050175. Any configuration of one or more helicases and one or more spacers disclosed in the International Application may be used in this invention.

When a part of the complementary polynucleotide enters the pore and moves through the pore along the field resulting from the applied potential, the one or more helicases are moved past the spacer by the pore as the polynucleotide moves through the pore. This is because the complementary polynucleotide (including the one or more spacers) moves through the pore and the one or more helicases remain on top of the pore.

The one or more spacers are preferably part of the complementary polynucleotide, for instance they interrupt(s) the polynucleotide sequence. The one or more spacers are preferably not part of one or more blocking molecules, such as speed bumps, hybridised to the polynucleotide.

There may be any number of spacers in the complementary polynucleotide, such as 1, 2, 3, 4, 5, 6, 7, 8, 9, 10 or more spacers. There are preferably two, four or six spacers in the polynucleotide. There may be one or more spacers in different regions of the polynucleotide, such as one or more spacers in the Y adaptor and/or hairpin loop adaptor.

The one or more spacers each provides an energy barrier which the one or more helicases cannot overcome even in the active mode. The one or more spacers may stall the one or more helicases by reducing the traction of the helicase (for instance by removing the bases from the nucleotides in the polynucleotide) or physically blocking movement of the one or more helicases (for instance using a bulky chemical group).

The one or more spacers may comprise any molecule or combination of molecules that stalls the one or more helicases. The one or more spacers may comprise any molecule or combination of molecules that prevents the one or more helicases from moving along the polynucleotide. It is straightforward to determine whether or not the one or more helicases are stalled at one or more spacers in the absence of a transmembrane pore and an applied potential. For instance, the ability of a helicase to move past a spacer and displace a complementary strand of DNA can be measured by PAGE.

The one or more spacers typically comprise a linear molecule, such as a polymer. The one or more spacers typically have a different structure from the polynucleotide. For instance, if the polynucleotide is DNA, the one or more spacers are typically not DNA. In particular, if the polynucleotide is deoxyribonucleic acid (DNA) or ribonucleic acid (RNA), the one or more spacers preferably comprise peptide nucleic acid (PNA), glycerol nucleic acid (GNA), threose nucleic acid (TNA), locked nucleic acid (LNA) or a synthetic polymer with nucleotide side chains. The one or more spacers may comprise one or more nucleotides in the opposite direction from the polynucleotide. For instance, the one or more spacers may comprise one or more nucleotides in the 3' to 5' direction when the polynucleotide is in the 5' to 3' direction. The nucleotides may be any of those discussed above.

The one or more spacers preferably comprises one or more nitroindoles, such as one or more 5-nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more Iso-deoxycytidines (Iso-dCs), one or more Iso-deoxyguanosines (Iso-dGs), one or more iSpC3 groups (i.e. nucleotides which lack sugar and a base), one or more photo-cleavable (PC) groups, one or more hexandiol groups, one or more spacer 9 (iSp9) groups, one or more spacer 18 (iSp18) groups, a polymer or one or more thiol connections. The one or more spacers may comprise any combination of these groups. Many of these groups are commercially available from IDT® (Integrated DNA Technologies®).

The one or more spacers may contain any number of these groups. For instance, for 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections, the one or more spacers preferably comprise 2, 3, 4, 5, 6, 7, 8, 9, 10, 11, 12 or more. The one or more spacers preferably comprise 2, 3, 4, 5, 6, 7, 8 or more iSp9 groups. The one or more spacers preferably comprise 2, 3, 4, 5 or 6 or more iSp18 groups. The most preferred spacer is four iSp18 groups.

The polymer is preferably a polypeptide or a polyethylene glycol (PEG). The polypeptide preferably comprises 2, 3, 4, 5, 6, 7, 8, 9, 10, 11, 12 or more amino acids. The PEG preferably comprises 2, 3, 4, 5, 6, 7, 8, 9, 10, 11, 12 or more monomer units.

The one or more spacers preferably comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide. Abasic spacers can be inserted into polynucleotides by removing the nucleobases from one or more adjacent nucleotides. For instance, polynucleotides may be modified to include 3-methyladenine, 7-methylguanine, 1,N6-ethenoadenine inosine or hypoxanthine and the nucleobases may be removed from these nucleotides using Human Alkyladenine DNA Glycosylase (hAAG). Alternatively, polynucleotides may be modified to include uracil and the nucleobases removed with Uracil-DNA Glycosylase (UDG). In one embodiment, the one or more spacers do not comprise any abasic nucleotides.

The one or more helicases may be stalled by (i.e. before) or on each linear molecule spacers. If linear molecule spacers are used, the polynucleotide is preferably provided with a double stranded region of polynucleotide adjacent to the end of each spacer past which the one or more helicases are to be moved. The double stranded region typically helps to stall the one or more helicases on the adjacent spacer. The presence of the double stranded region(s) is particularly preferred if the method is carried out at a salt concentration of about 100 mM or lower. Each double stranded region is typically at least 10, such as at least 12, nucleotides in length. If the polynucleotide used in the invention is single stranded, a double stranded region may formed by hybridising a shorter polynucleotide to a region adjacent to a spacer. The shorter polynucleotide is typically formed from the same nucleotides as the polynucleotide, but may be formed from different nucleotides. For instance, the shorter polynucleotide may be formed from LNA.

If linear molecule spacers are used, the polynucleotide is preferably provided with a blocking molecule at the end of each spacer opposite to end past which the one or more helicases are to be moved. In other words, the helicase is stalled between a blocking molecule and a spacer. This can help to ensure that the one or more helicases remain stalled on each spacer. It may also help retain the one or more helicases on the polynucleotide in the case that it/they diffuse(s) off in solution. The blocking molecule may be any of the chemical groups discussed below which physically cause the one or more helicases to stall. The blocking molecule may be a double stranded region of polynucleotide.

The one or more spacers preferably comprise one or more chemical groups which physically cause the one or more helicases to stall. The one or more chemical groups are preferably one or more pendant chemical groups. The one or more chemical groups may be attached to one or more nucleobases in the polynucleotide. The one or more chemical groups may be attached to the polynucleotide backbone. Any number of these chemical groups may be present, such as 2, 3, 4, 5, 6, 7, 8, 9, 10, 11, 12 or more. Suitable groups include, but are not limited to, fluorophores, streptavidin and/or biotin, cholesterol, methylene blue, dinitrophenols (DNPs), digoxigenin and/or anti-digoxigenin and dibenzylcyclooctyne groups.

Different spacers in the polynucleotide may comprise different stalling molecules. For instance, one spacer may comprise one of the linear molecules discussed above and another spacer may comprise one or more chemical groups which physically cause the one or more helicases to stall. A spacer may comprise any of the linear molecules discussed above and one or more chemical groups which physically cause the one or more helicases to stall, such as one or more abasics and a fluorophore.

Suitable spacers can be designed depending on the type of polynucleotide and the conditions under which the method of the invention is carried out. Most helicases bind and move along DNA and so may be stalled using anything that is not DNA. Suitable molecules are discussed above.

The method of the invention is preferably carried out in the presence of free nucleotides and/or the presence of a helicase cofactor. This is discussed in more detail below. In the absence of the transmembrane pore and an applied potential, the one or more spacers are preferably capable of stalling the one or more helicases in the presence of free nucleotides and/or the presence of a helicase cofactor.

If the method of the invention is carried out in the presence of free nucleotides and a helicase cofactor as discussed below (such that the one of more helicases are in the active mode), one or more longer spacers are typically used to ensure that the one or more helicases are stalled on the polynucleotide before they are contacted with the transmembrane pore and a potential is applied. One or more shorter spacers may be used in the absence of free nucleotides and a helicase cofactor (such that the one or more helicases are in the inactive mode).

The salt concentration also affects the ability of the one or more spacers to stall the one or more helicases. In the absence of the transmembrane pore and an applied potential, the one or more spacers are preferably capable of stalling the one or more helicases at a salt concentration of about 100 mM or lower. The higher the salt concentration used in the method of the invention, the shorter the one or more spacers that are typically used and vice versa.

Preferred combinations of features are shown in the Table 4 below.

| Polynucleotide | Spacer composition* | Spacer length (i.e. number of*) | Salt [ ] | Free nucleotides? | Helicase cofactor? |
|---|---|---|---|---|---|
| DNA | iSpC3 | 4 | 1M | Yes | Yes |
| DNA | iSp18 | 4 | 100-1000 mM | Yes | Yes |
| DNA | iSp18 | 6 | <100-1000 mM | Yes | Yes |

-continued

| Polynucleotide | Spacer composition* | Spacer length (i.e. number of*) | Salt [ ] | Free nucleotides? | Helicase cofactor? |
|---|---|---|---|---|---|
| DNA | iSp18 | 2 | 1M | Yes | Yes |
| DNA | iSpC3 | 12 | <100-1000 mM | Yes | Yes |
| DNA | iSpC3 | 20 | <100-1000 mM | Yes | Yes |
| DNA | iSp9 | 6 | 100-1000 mM | Yes | Yes |
| DNA | idSp | 4 | 1M | Yes | Yes |

The method may concern moving two or more helicases past a spacer. In such instances, the length of the spacer is typically increased to prevent the trailing helicase from pushing the leading helicase past the spacer in the absence of the pore and applied potential. If the method concerns moving two or more helicases past one or more spacers, the spacer lengths discussed above may be increased at least 1.5 fold, such 2 fold, 2.5 fold or 3 fold. For instance, if the method concerns moving two or more helicases past one or more spacers, the spacer lengths in the third column of Table 4 above may be increased 1.5 fold, 2 fold, 2.5 fold or 3 fold.

Bridging Moiety

In a preferred embodiment, the complementary polynucleotide is linked to the target RNA using a bridging moiety. As discussed above, step (a) preferably comprises hybridising a primer to the target RNA and using the primer to form the complementary polynucleotide. The primer preferably comprises a bridging moiety and the bridging moiety is preferably attached to the target RNA such that the complementary polynucleotide linked to the target RNA. Step (b) preferably comprises contacting the linked construct comprising the complementary polynucleotide and the target RNA with a transmembrane pore such that such that both the complementary polynucleotide and the target RNA move through the pore. The complementary polynucleotide is preferably contacted with the pore before the target RNA. Step c) preferably comprises taking one or more measurements as both the complementary polynucleotide and the target RNA move with respect to the pore wherein the measurements are indicative of one or more characteristics of the complementary polynucleotide and the target RNA and thereby characterising the target double stranded polynucleotide.

Linking and interrogating both the complementary polynucleotide and the target RNA in this way increases the efficiency and accuracy of characterization.

The bridging moiety is capable of linking the two strands of the target polynucleotide. The bridging moiety typically covalently links the two strands of the target polynucleotide. The bridging moiety can be anything that is capable of linking the two strands of the target polynucleotide, provided that the bridging moiety does not interfere with movement of the single stranded polynucleotide through the transmembrane pore.

The bridging moiety may be linked to the target polynucleotide by any suitable means known in the art. The bridging moiety may be synthesized separately and chemically attached or enzymatically ligated to the target polynucleotide. Alternatively, the bridging moiety may be generated in the processing of the target polynucleotide.

The bridging moiety is linked to the target polynucleotide at or near one end of the target polynucleotide. The bridging moiety is preferably linked to the target polynucleotide within 10 nucleotides of the end of the target polynucleotide Suitable bridging moieties include, but are not limited to a polymeric linker, a chemical linker, a polynucleotide or a polypeptide. Preferably, the bridging moiety comprises DNA, RNA, modified DNA (such as abasic DNA), RNA, PNA, LNA or PEG. The bridging moiety is more preferably DNA or RNA.

The bridging moiety is most preferably a hairpin loop or a hairpin loop adaptor. Suitable hairpin adaptors can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below.

The hairpin adaptor may be ligated to either end of the complementary polynucleotide and/or target RNA, i.e. the 5' or the 3' end. The hairpin adaptor may be ligated using any method known in the art. The hairpin adaptor may be ligated using a ligase, such as T4 DNA ligase, E. coli DNA ligase, Taq DNA ligase, Tma DNA ligase and 9° N DNA ligase.

The complementary polynucleotide and the target RNA may be separated as or before the linked construct is contacted with the pore in accordance with the invention. They may be separated as the polynucleotide movement through the pore is controlled by a polynucleotide binding protein, such as a helicase, or molecular brake.

The complementary polynucleotide and the target RNA may be separated using any method known in the art. For instance, they may be separated by a polynucleotide binding protein or using conditions which favour dehybridsation (examples of conditions which favour dehybridisation include, but are not limited to, high temperature, high pH and the addition of agents that can disrupt hydrogen bonding or base pairing, such as formamide and urea).

The hairpin adaptor preferably comprises a selectable binding moiety. This allows the linked construct to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologus sequences. Alternatively, selectable polynucleotide sequences specifically bind to a surface coated with polynucleotide binding proteins.

The hairpin adaptor and/or the selectable binding moiety may comprise a region that can be cut, nicked, cleaved or hydrolysed. Such a region can be designed to allow the complementary polynucleotide and/or target RNA to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

The linked construct preferably comprises a leader sequence at the opposite end from the bridging moiety, such as a hairpin loop or hairpin loop adaptor. Leader sequences are discussed in more detail below.

Leader Sequence

Before the contacting step, the method preferably comprises attaching to the linked construct a leader sequence which preferentially threads into the pore. The leader sequence facilitates the method of the invention. The leader sequence is designed to preferentially thread into the pore of the invention and thereby facilitate the movement of polynucleotide through the pore. The leader sequence can also be used to link the construct to the one or more anchors as discussed above. The leader sequence may be linked to the complementary polynucleotide or the target RNA.

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

The leader sequence is preferably part of a Y adaptor as defined below.

Double Coupling

The method of the invention may involve double coupling of the complementary polynucleotide and target RNA. In a preferred embodiment, the method of the invention comprises:

(a) providing the complementary polynucleotide and target RNA with a Y adaptor at one end and a bridging moiety adaptor, such as a hairpin loop adaptor, at the other end, wherein the Y adaptor comprises one or more first anchors for coupling the polynucleotide to the membrane, wherein the hairpin loop adaptor comprises one or more second anchors for coupling the polynucleotide to the membrane and wherein the strength of coupling of the hairpin loop adaptor to the membrane is greater than the strength of coupling of the Y adaptor to the membrane;

(b) contacting the polynucleotide provided in step (a) with the pore the invention such that the polynucleotide moves through the pore; and (c) taking one or more measurements as the polynucleotide moves with respect to the pore, wherein the measurements are indicative of one or more characteristics of the polynucleotide, and thereby characterising the target polynucleotide.

This type of method is discussed in detail in the UK Application No. 1406147.7.

The double stranded polynucleotide is provided with a Y adaptor at one end and a hairpin loop adaptor at the other end. The Y adaptor and/or the hairpin adaptor are typically polynucleotide adaptors. They may be formed from any of the polynucleotides discussed above.

The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor comprises the one or more first anchors. Anchors are discussed in more detail above.

The Y adaptor preferably comprises a leader sequence which preferentially threads into the pore. This is discussed above.

The hairpin adaptor preferably comprises a selectable binding moiety as discussed above. The hairpin adaptor and/or the selectable binding moiety may comprise a region that can be cut, nicked, cleaved or hydrolysed as discussed above.

If one or more helicases and one or more molecular brakes are used as discussed above, the Y adaptor preferably comprises the one or more helicases and the hairpin loop adaptor preferably comprises the one or more molecular brakes.

The Y adaptor and/or the hairpin adaptor may be ligated to the polynucleotide using any method known in the art. One or both of the adaptors may be ligated using a ligase, such as T4 DNA ligase, $E.\ coli$ DNA ligase, Taq DNA ligase, Tma DNA ligase and 9° N DNA ligase. Alternatively, the adaptors may be added to the polynucleotide using the methods of the invention discussed below.

In a preferred embodiment, step a) of the method comprises modifying the double stranded polynucleotide so that it comprises the Y adaptor at one end and the hairpin loop adaptor at the other end. Any manner of modification can be used. The methods of modification and characterisation may be combined in any way.

The strength of coupling (or binding) of the bridging moiety (or hairpin) adaptor to the membrane is greater than the strength of coupling (or binding) of the Y adaptor to the membrane. This can be measured in any way. A suitable method for measuring the strength of coupling (or binding) is disclosed in the Examples of the UK Application No. 1406147.7.

The strength of coupling (or binding) of the hairpin loop adaptor is preferably at least 1.5 times the strength of coupling (or binding) of the hairpin loop adaptor, such as at least twice, at least three times, at least four times, at least five or at least ten times the strength of coupling (or binding) of the anchor adaptor. The affinity constant (Kd) of the hairpin loop adaptor for the membrane is preferably at least 1.5 times the affinity constant of the Y adaptor, such as at least twice, at least three times, at least four times, at least five or at least ten times the strength of coupling of the Y adaptor.

There are several ways in which the hairpin loop adaptor couples (or binds) more strongly to the membrane than the Y adaptor. For instance, the hairpin loop adaptor may comprise more anchors than the Y adaptor. For instance, the hairpin loop adaptor may comprise 2, 3 or more second anchors whereas the Y adaptor may comprise one first anchor.

The strength of coupling (or binding) of the one or more second anchors to the membrane may be greater than the strength of coupling (or binding) of the one or more first anchors to the membrane. The strength of coupling (or binding) of the one or more second anchors to the hairpin loop adaptor may be greater than the strength of coupling (or binding) of the one or more first anchors to the Y adaptor. The one or more first anchors and the one or more second anchors may be attached to their respective adaptors via hybridisation and the strength of hybridisation is greater in the one or more second anchors than in the one or more first anchors. Any combination of these embodiments may also be used in the invention. Strength of coupling (or binding) may be measure using known techniques in the art.

The one or more second anchors preferably comprise one or more groups which couples(s) (or bind(s)) to the membrane with a greater strength than the one or more groups in the one or more first anchors which couple(s) (or bind(s)) to the membrane. In preferred embodiments, the hairpin loop adaptor/one or more second anchors couple (or bind) to the membrane using cholesterol and the Y adaptor/one or more first anchors couple (or bind) to the membrane using palmitate. Cholesterol binds to triblock copolymer membranes and lipid membranes more strongly than palmitate. In an alternative embodiment, the hairpin loop adaptor/one or more second anchors couple (or bind) to the membrane using a mono-acyl species, such as palmitate, and the Y adaptor/one or more first anchors couple (or bind) to the membrane using a diacyl species, such as dipalmitoylphosphatidylcholine.

Diagnosing or Prognosing Diseases or Conditions mRNA is preferably used in the invention to diagnose or prognose a disease or condition. Some diseases or conditions are associated with an altered amount (or level) of mRNA. The mRNA may be normal or wild-type mRNA, i.e. not alternately spliced. The amount (or level) of the mRNA may be increased or decreased in the disease or condition compared with the amount (or level) in a patient without the disease or condition. Such diseases or conditions may be diagnosed or prognosed by determining the amount of the mRNA in a sample from the patient using a method of the invention.

Many genetic diseases or conditions are caused by mutations that cause alternate mRNA splicing, such as mRNA splicing defects. A number of diseases or conditions are associated with alternate mRNA splicing which are not attributed to overt mutations. The presence or absence of alternate splicing can be identified by determining the presence or absence of an alternately spliced mRNA in a sample from the patient using the method of the invention. In some instances, alternate mRNA splicing may be the normal function of a cell. In such instances, an increased or decreased amount (or level) of the alternately spliced mRNA compared with the normal amount (i.e. the amount in a patient without the disease or condition) may be used to diagnose or prognose the disease or condition.

The invention provides a method of diagnosing or prognosing a disease or condition associated with an altered amount and/or alternate splicing of messenger RNA (mRNA) in a patient. The invention provides a method of determining whether or not a patient has or is at risk of developing a disease or condition associated with an altered amount and/or alternate splicing of messenger RNA (mRNA). In each instance, the method comprises determining the amount and/or identity of the mRNA in a sample from the patient using a method of the invention. The disease or condition may be any of those discussed below. The disease or condition is preferably cystic fibrosis, familial dysautonomia, frontotemporal lobar dementia, amyotrophic lateral sclerosis, Hutchinson-Gilford progeria syndrome, medium-chain acyl-CoA dehydrogenase (MCAD) deficiency, myotonic dystrophy, Prader-Willi syndrome, spinal muscular atrophy, tauopathy, hypercholesterolemia or cancer. These diseases, their causes and possible treatments are discussed in Tazi et al. (Biochimica et Biophysica Acta (BBA)—Molecular Basis of Disease, Volume 1792, Issue 1, January 2009, Pages 14-26).

The presence of an altered (i.e. increased or decreased) amount (or level) of the mRNA in the sample from the patient typically diagnoses or prognoses the disease or condition, i.e. indicates that the patient has or is at risk of developing the disease or condition. The absence of an altered (i.e. increased or decreased) amount (or level) of the mRNA in the sample from the patient typically indicates that the patient does not have or is not at risk of developing the disease or condition. The amount of mRNA can be determined as discussed above.

The presence of the alternately spliced mRNA in the sample from the patient typically diagnoses or prognoses the disease or condition, i.e. indicates that the patient has or is at risk of developing the disease or condition. The absence of the alternately spliced mRNA in the sample from the patient typically indicates that the patient does not have or is not at risk of developing the disease or condition. The presence or absence of the alternately spliced mRNA can be determined by identifying RNA in the sample as discussed above.

An increased or decreased amount (or level) of the alternately spliced mRNA in the sample from the patient typically diagnoses or prognoses the disease or condition, i.e. indicates that the patient has or is at risk of developing the disease or condition. No change in the amount of the alternately spliced mRNA in the sample from the patient (compared with the amount or level in a patient without the disease or condition) typically indicates that the patient does not have or is not at risk of developing the disease or condition. The amount of the alternately spliced mRNA can be determined as discussed above.

miRNA is preferably used in the invention to diagnose or prognose a disease or condition. The invention provides a method of diagnosing or prognosing a disease or condition associated with a miRNA. The invention provides a method of determining whether or not a patient has or is at risk of developing a disease or condition associated with a miRNA. The method comprises determining the presence or absence of the miRNA in a sample from the patient using a method of the invention. The disease or condition may be any of those discussed below.

The presence of the miRNA in the sample from the patient typically indicates that the patient has or is at risk of developing the disease or condition. The absence of the miRNA in the sample from the patient typically indicates that the patient does not have or is not at risk of developing the disease or condition. The presence or absence of the miRNA can be determined by identifying any miRNAs in the sample as discussed above.

The disease or condition is preferably cancer, coronary heart disease, cardiovascular disease or sepsis. The disease or condition is more preferably abdominal aortic aneurysm, acute lymphoblastic leukemia (ALL), acute myeloid leukemia (AML), acute myocardial infarction, acute promyelocytic leukemia (APL), adenoma, adrenocortical carcinoma, alcoholic liver disease, Alzheimer's disease, anaplastic thyroid carcinoma (ATC), anxiety disorder, asthma, astrocytoma, atopic dermatitis, autism spectrum disorder (ASD), B-cell chronic lymphocytic leukemia, B-cell lymphoma, Becker muscular dystrophy (BMD), bladder cancer, brain neoplasm, breast cancer, Burkitt lymphoma, cardiac hypertrophy, cardiomyopathy, cardiovascular disease, cerebellar neurodegeneration, cervical cancer, cholangiocarcinoma, cholesteatoma, choriocarcinoma, chronic lymphocytic leukemia, chronic myeloid leukemia, chronic pancreatitis, colon carcinoma, colorectal cancer, congenital heart disease, coronary artery disease, cowden syndrome, dermatomyositis (DM), diabetic nephropathy, diarrhea predominant irritable bowel syndrome, diffuse large B-cell lymphoma, dilated cardiomyopathy, down syndrome (DS), duchenne muscular dystrophy (DMD), endometrial cancer, endometrial endometrioid adenocarcinoma, endometriosis, epithelial ovarian cancer, esophageal cancer, esophagus squamous cell carcinoma, essential thrombocythemia (ET), facioscapulohumeral muscular dystrophy (FSHD), follicular lymphoma (FL), follicular thyroid carcinoma (FTC), frontotemporal dementia, gastric cancer (stomach cancer), glioblastoma, glioblastoma multiforme (GBM), glioma, glomerular disease, glomerulosclerosis, hamartoma, HBV-related cirrhosis, HCV infection, head and neck cancer, head and neck squamous cell carcinoma (HNSCC), hearing loss, heart disease, heart failure, hepatitis B, hepatitis C, hepatocellular carcinoma (HCC), hilar cholangiocarcinoma, Hodgkin's lymphoma, homozygous sickle cell disease (HbSS), Huntington's disease (HD), hypertension, hypopharyngeal cancer, inclusion body myositis (IBM), insulinoma, intrahepatic cholangiocarcinoma (ICC), kidney cancer, kidney disease, laryngeal carcinoma, late insomnia (sleep disease), leiomyoma of lung, leukemia, limb-girdle muscular dystrophies types 2A (LGMD2A), lipoma, lung adenocarcinoma, lung cancer, lymphoproliferative disease, malignant lymphoma, malignant melanoma, malignant mesothelioma (MM), mantle cell lymphoma (MCL), medulloblastoma, melanoma, meningioma, metabolic disease, miyoshi myopathy (MM), multiple myeloma (MM), multiple sclerosis, MYC-rearranged lymphoma, myelodysplastic syndrome, myeloproliferative disorder, myocardial infarction, myocardial injury, myoma, nasopharyngeal carcinoma (NPC), nemaline myopathy (NM), nephritis, neuroblastoma (NB), neutrophilia, Niemann-Pick type C (NPC) disease, non-alcoholic fatty liver disease (NAFLD), non-small cell lung cancer (NSCLC), obesity, oral carcinomaosteosarcoma ovarian cancer (OC), pancreatic cancer, pancreatic ductal adenocarcinoma (PDAC), pancreatic neoplasia, panic disease, papillary thyroid carcinoma (PTC), Parkinson's disease, PFV-1 infection, pharyngeal disease, pituitary adenoma, polycystic kidney disease, polycystic liver disease, polycythemia vera (PV), polymyositis (PM), primary biliary cirrhosis (PBC), primary myelofibrosis, prion disease, prostate cancer, psoriasic arthritis, psoriasis, pulmonary hypertension, recurrent ovarian cancer, renal cell carcinoma, renal clear cell carcinoma, retinitis pigmentosa (RP), retinoblastoma, rhabdomyosarcoma, rheumatic heart disease and atrial fibrillation, rheumatoid arthritis, sarcoma, schizophrenia, sepsis, serous ovarian cancer, Sezary syndrome, skin disease, small cell lung cancer, spinocerebellar ataxia, squamous carcinoma, T-cell leukemia, teratocarcinoma, testicular germ cell tumor, thalassemia, thyroid cancer, tongue squamous cell carcinoma, tourette's syndrome, type 2 diabetes, ulcerative colitis (UC), uterine leiomyoma (ULM), uveal melanoma, vascular disease, vesicular stomatitis or Waldenstrom macroglobulinemia (WM).

The patient may be any of the mammals discussed above. The patient is preferably human. The patient is an individual.

The sample may be any of those discussed above. The sample is typically from any tissue or bodily fluid. The sample typically comprises a body fluid and/or cells of the patient and may, for example, be obtained using a swab, such as a mouth swab. The sample may be, or be derived from, blood, urine, saliva, skin, cheek cell or hair root samples. The target RNA is typically extracted from the sample before it is used in the method of the invention.

The method may concern diagnosis of the disease or condition in the patient, i.e. determining whether or not the patient has the disease or condition. The patient may be symptomatic.

The method may concern prognosing the disease or condition in the patient, i.e. determining whether or not the patient is likely to develop the disease or condition. The patient can be asymptomatic. The patient can have a genetic predisposition to the disease or condition. The patient may have one or more family member(s) with the disease or condition.

Kits

The invention also provides a kit for characterising a target RNA. The kit comprises (a) a transmembrane pore and (b) a reverse transcriptase enzyme and/or a reverse transcription primer. Any of the embodiments discussed above with reference to the method of the invention equally apply to the kits.

The kit may further comprise the components of a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit typically comprises nucleotides. The kit preferably comprises dAMP, dTMP, dGMP and dCMP. The kit preferably does not comprise means to amplify and/or express polynucleotides.

Apparatus

The invention also provides an apparatus for characterising target RNAs. The apparatus comprises (a) a plurality of pores and (b) a plurality of a plurality of reverse transcriptase enzymes and/or a plurality of reverse transcription primers. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention.

The apparatus is preferably set up to carry out the method of the invention.

The apparatus preferably comprises:

a sensor device that is capable of supporting the plurality of pores and being operable to perform RNA characterisation using the pores and the helicases or constructs; and at least one reservoir for holding material for performing the characterisation.

The apparatus preferably comprises:

a sensor device that is capable of supporting the plurality of pores and being operable to perform RNA characterisation using the pores and the helicases or constructs; and at least one port for delivery of the material for performing the characterisation.

The apparatus preferably comprises:

a sensor device that is capable of supporting the membrane and plurality of pores and being operable to perform RNA characterising using the pores;

at least one reservoir for holding material for performing the characterising;

a fluidics system configured to controllably supply material from the at least one reservoir to the sensor device; and one or more containers for receiving respective samples, the fluidics system being configured to supply the samples selectively from one or more containers to the sensor device. The apparatus may be any of those described in International Application No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312). The following Examples illustrates the invention.

Example 1

This example describes the sample preparation procedure used to produce the cDNA which can then be characterised using the nanopore system. The steps of the procedure outlined in this example are steps A to C shown in FIG. 1.
Materials and Methods Complementary DNA (cDNA, SEQ ID NO: 11) was reverse transcribed from messenger RNA (SEQ ID NO: 8, mRNA) by SuperScript II Reverse Transcriptase (Life Technologies) using an adaption of the standard SuperScript II protocol (the protocol that was followed is shown below).
Protocol

| Reagent | Add | Stock Concentration | Final Concentration |
|---|---|---|---|
| mRNA (SEQ ID NO: 8) | 3.5 ul | 1 mg/ml | |
| Custom pT Primer (SEQ ID NO: 9 attached at its 3' end to four iSpC3 spacers which are attached to the 5' end of SEQ ID NO: 10) | 1.1 ul | 10 uM | 550 nM |
| dNTP Mix | 1 ul | 10 mM Ea | 0.5 mM Ea |
| 5x Superscript II Buffer | 4 ul | 5x | 1x |
| DTT | 2 ul | 0.1M | 10 mM |
| Superscript II | 1 ul | | |
| Nuclease Free H2O | 7.4 ul | | |
| Total | 20 ul | | |

The mRNA (SEQ ID NO: 8), custom pT primer (SEQ ID NO: 9 attached at its 3' end to four iSpC3 spacers which are attached to the 5' end of SEQ ID NO: 10), dNTP mix and nuclease free water were mixed together and then heated to 65° C. for 5 minutes before being quick chilled on ice. 5× SuperScript II buffer and DTT were then added to the mixture and the sample incubated at 42° C. for 2 minutes. Finally, Superscript II was added to the reaction mixture and then the sample was incubated at 42° C. for 50 mins and then at 70° C. for 15 minutes. The cDNA product (SEQ ID NO: 11 attached at its 5' end to the 3' end of SEQ ID NO: 10 which is attached by its 5' end to four iSpC3 spacers which are attached to the 3' end of SEQ ID NO: 9) hybridised to the mRNA (SEQ ID NO: 8) was then purified using SPRI beads (Agencourt AMPure).

Both the starting mRNA material (SEQ ID NO: 8) and the cDNA product (SEQ ID NO: 11 attached at its 5' end to the 3' end of SEQ ID NO: 10 which is attached by its 5' end to four iSpC3 spacers which are attached to the 3' end of SEQ ID NO: 9, where SEQ ID NO: 11 is hybridised to SEQ ID NO: 8) were analysed for mass/vol and DNA-RNA hybrid length using a Nanodrop and Agilent BioAnalyzer (12 k Agilent Chip).

This procedure was also used to produce cDNA by reverse transcribing mRNA from yeast (used in Example 3). In the above protocol mRNA (SEQ ID NO: 8) was replaced with *Saccharomyces cerevisiae* PolyA+ messenger RNA (1 mg/ml), which was purchased from Clontech and used as received.

Example 2

Figure 2:
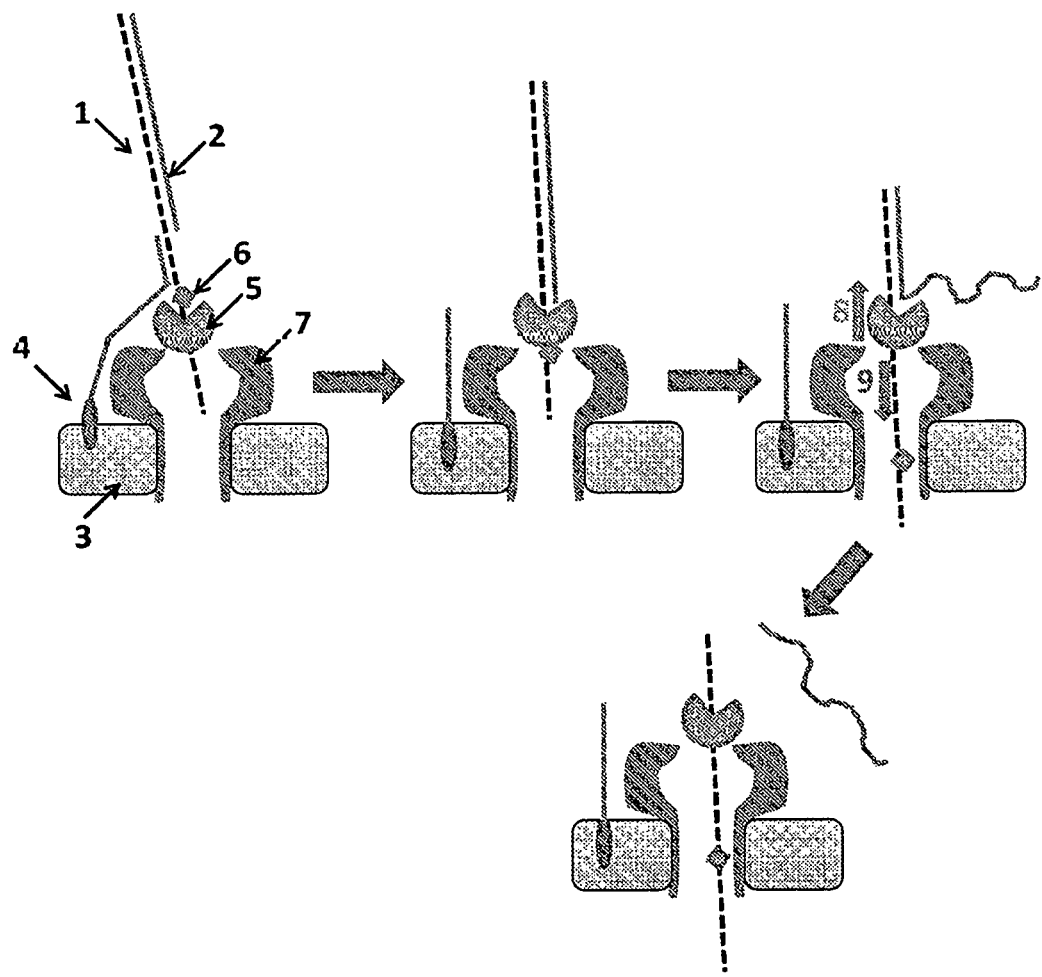
FIG. 2 shows the nanopore system used in Example 2 and 3 to characterise cDNA. The cDNA/mRNA (cDNA labelled 1, mRNA labelled 2) are tethered to the bilayer (labelled 3) by a short strand of DNA with a 3' cholesterol tether (labelled 4). The leader sequence of the cDNA allows the enzyme (labelled 5) to bind to the cDNA but the iSpC3 spacers (shown as a square and labelled 6) stall the enzyme on the DNA until the DNA enters the nanopore (labelled 7). The enzyme moves along the cDNA, controlling the movement through the nanopore. The mRNA dehybridises from the complementary cDNA as the enzyme moves along the cDNA. The direction of movement of the enzyme is indicated by the arrow labelled 8 and the direction of movement of the cDNA is indicated by the arrow labelled 9.

This example describes the characterisation of cDNA (SEQ ID NO: 11 attached at its 5' end to the 3' end of SEQ ID NO: 10 which is attached by its 5' end to four iSpC3 spacers which are attached to the 3' end of SEQ ID NO: 9) using a nanopore system. See FIG. 2 for a cartoon representation of the system.
Materials and Methods Prior to setting up the experiment, cDNA/mRNA (0.05 nM, SEQ ID NO: 11 attached at its 5' end to the 3' end of SEQ ID NO: 10 which is attached by its 5' end to four iSpC3 spacers which are attached to the 3' end of SEQ ID NO: 9, where SEQ ID NO: 11 is hybridised to SEQ ID NO: 8) was hybridised to the tether (0.25 nM, SEQ ID NO: 12) by heating the sample at 40° C. in buffer (10 mM TRIS, 50 mM NaCl, pH7.5) for two minutes and then slow cooling to 30° C. over 15 minutes. This is shown as step D in FIG. 1. The cDNA/mRNA sample was then pre-incubated with T4 Dda-E94C/A360C (125 nM, SEQ ID NO: 13 with mutations E94C/A360C) for an hour at room temperature in buffer (126.5 mM KCl, 25 mM NaCl, 25 mM potassium phosphate pH 7.5-8.0 and 5 mM Tris).

Electrical measurements were acquired at 25-30° C. from single MspA nanopores (MS(B1-G75S/G77S/L88N/Q126R)8 MspA (SEQ ID NO: 2 with mutations G75S/G77S/L88N/Q126R) inserted in block co-polymer in buffer (600 mM KCl, 25 mM potassium phosphate, 75 mM Potassium Ferrocyanide (II), 25 mM Potassium ferricyanide (III), pH 8). After achieving a single pore inserted in the block co-polymer, then buffer (1 mL, 600 mM KCl, 25 mM potassium phosphate, 75 mM Potassium Ferrocyanide (II), 25 mM Potassium ferricyanide (III), pH 8) was flowed through the system to remove any excess MspA nanopores (MS(B1-G75S/G77S/L88N/Q126R)8 MspA (SEQ ID NO: 2 with mutations G75S/G77S/L88N/Q126R). MgCl$_2$ (10 mM final concentration) and ATP (5 mM final concentration) were mixed together with buffer (600 mM KCl, 25 mM potassium phosphate, 75 mM Potassium Ferrocyanide (II), 25 mM Potassium ferricyanide (III), pH 8) and then added to the cDNA/mRNA (0.05 nM final concentration), T4 Dda-E94C/A360C (1 nM final concentration, SEQ ID NO: 13 with mutations E94C/A360C) pre-mix. The pre-mix was then added to the nanopore experimental system. Experiments were carried out for eighteen hours at an applied potential of +120 mV and helicase-controlled cDNA movement was monitored.

Results and Discussion

Figure 3:
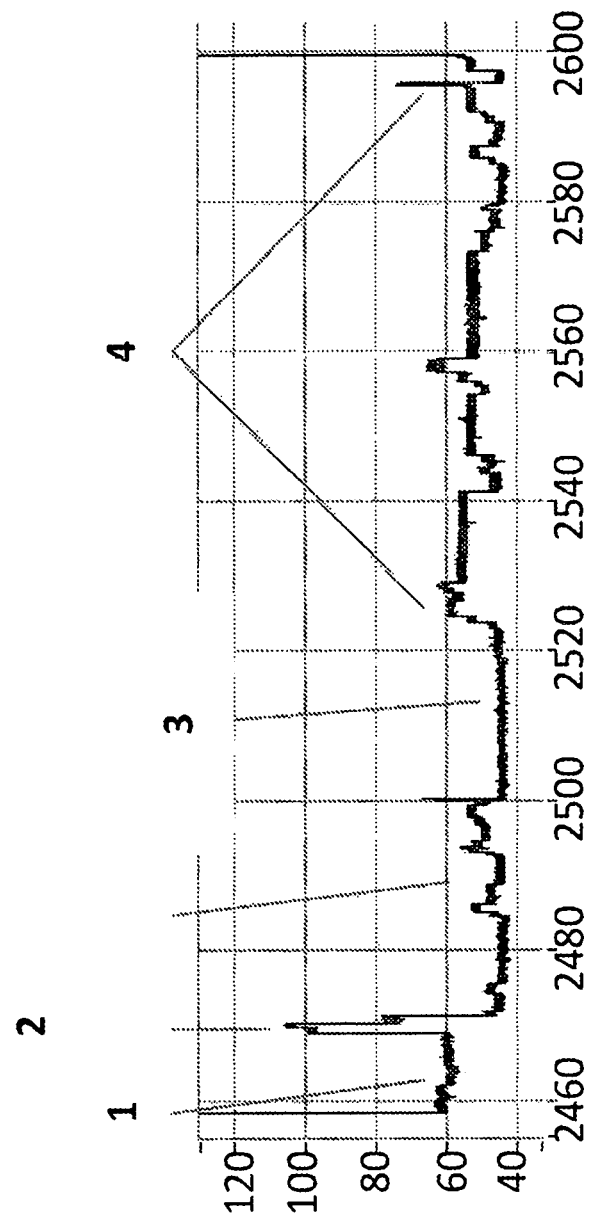
FIG. 3 shows an example current trace (y-axis label= Current (pA, 40 to 120), x-axis label=Time (s, 2460 to 2600)) of when a helicase (T4 Dda E94C/A360C (SEQ ID NO: 13 with mutations E94C/A360C)) controls the translocation of cDNA (0.05 nM, SEQ ID NO: 11 attached at its 5' end to the 3' end of SEQ ID NO: 10 which is attached by its 5' end to four iSpC3 spacers which are attached to the 3' end of SEQ ID NO: 9, where SEQ ID NO: 11 is hybridised to SEQ ID NO: 8) through a nanopore (MS(B1-G75S/G77S/L88N/Q126R)8 MspA (SEQ ID NO: 2 with mutations G75S/G77S/L88N/Q126R)). A number of features in the electrical read out are identified as the helicase controls the cDNA movement through the nanopore (label 1=capture tail, 2=the iSpC3 spacers in the primer, 3=polyT primer for the reverse transcriptase and 4=region of cDNA).

Helicase controlled DNA movement was observed for the cDNA (SEQ ID NO: 11 attached at its 5' end to the 3' end of SEQ ID NO: 10 which is attached by its 5' end to four iSpC3 spacers which are attached to the 3' end of SEQ ID NO: 9, where SEQ ID NO: 11 is hybridised to SEQ ID NO: 8). An example of a helicase-controlled DNA movement is shown in FIG. 3. A number of features in the electrical read out are identified as the helicase controls the cDNA movement through the nanopore. The region labelled 1 corresponds to the capture tail, the region labelled 2 corresponds to the iSpC3 spacers in the primer, the region labelled 3 corresponds to the polyT primer for the reverse transcriptase and the region labelled 4 corresponds to of the cDNA region. This example shows characterisation of cDNA which was transcribed from mRNA (SEQ ID NO: 8) as described in Example 1.

Example 3

This example describes the characterisation of cDNA using a nanopore system, where the cDNA was transcribed from mRNA found in yeast (*Saccharomyces cerevisiae*). See FIG. 2 for a cartoon representation of the system.

Materials and Methods

The materials and methods procedure described in Example 2 was repeated for the cDNA (0.05 nM) transcribed from yeast (*Saccharomyces cerevisiae*).

Results and Discussion

Figure 4:
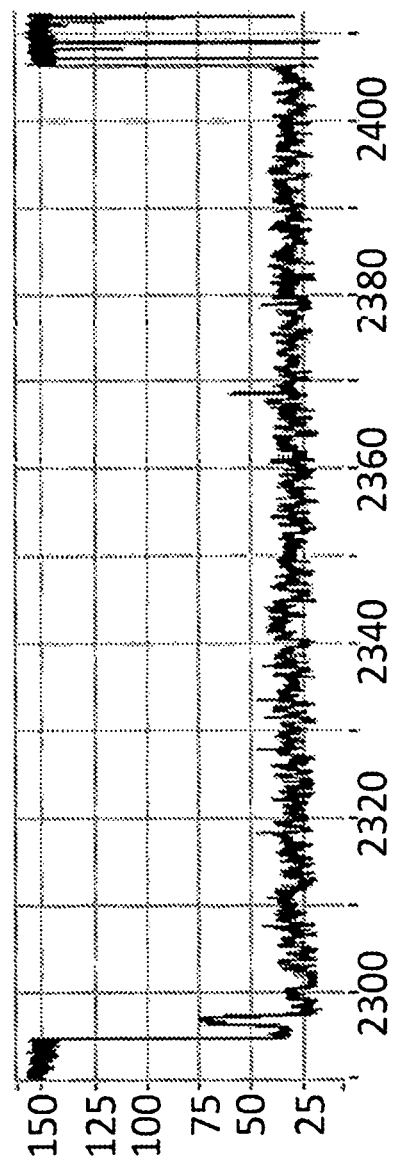
FIG. 4 shows an example current trace (y-axis label= Current (pA, 25 to 150), x-axis label=Time (s, 2300 to 2400)) of when a helicase (T4 Dda E94C/A360C (SEQ ID NO: 13 with mutations E94C/A360C)) controls the translocation of cDNA (0.05 nM) transcribed from yeast mRNA through a nanopore (MS(B1-G75S/G77S/L88N/Q126R)8 MspA (SEQ ID NO: 2 with mutations G75S/G77S/L88N/Q126R)).
Figure 5:
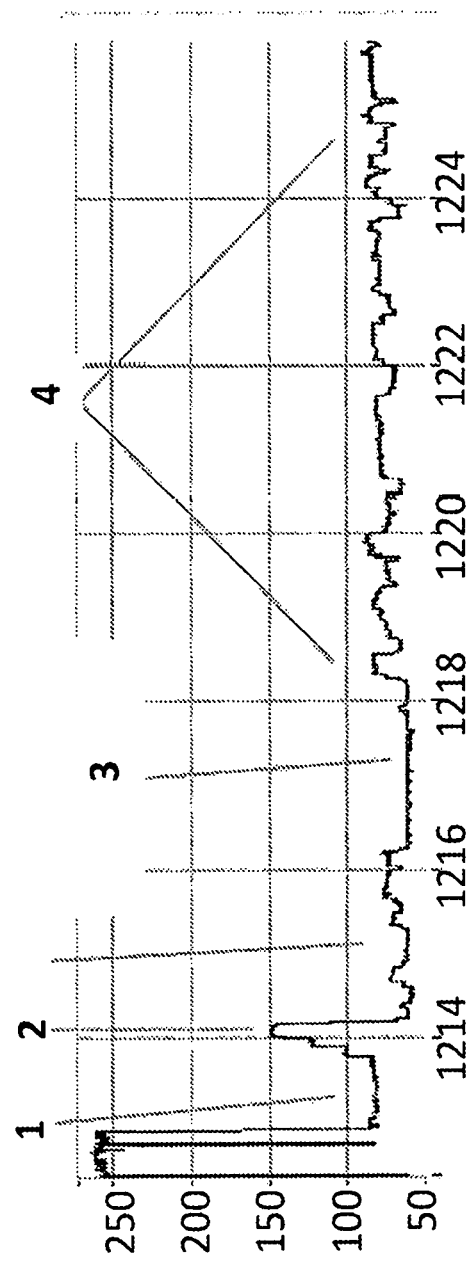
FIG. 5 shows a zoomed in region of an example current trace (y-axis label=Current (pA, 50 to 250), x-axis label=Time (s, 1214 to 1224)) of when a helicase (T4 Dda E94C/A360C (SEQ ID NO: 13 with mutations E94C/A360C)) controls the translocation of cDNA (0.05 nM) transcribed from yeast mRNA through a nanopore (MS(B1-G75S/G77S/L88N/Q126R)8 MspA (SEQ ID NO: 2 with mutations G75S/G77S/L88N/Q126R)). A number of features in the electrical read out are identified as the helicase controls the cDNA movement through the nanopore (label 1=capture tail, 2=the iSpC3 spacers in the primer, 3=polyT primer for the reverse transcriptase and 4=region of cDNA).

Enzyme-controlled translocation of cDNA through the nanopore was observed for cDNA transcribed from yeast (*Saccharomyces cerevisiae*) polyA+ mRNA. Examples of helicase-controlled translocation of cDNA from yeast are shown in FIGS. 4 and 5. FIG. 4 shows an example of a complete yeast cDNA trace. FIG. 5 shows the beginning of a yeast cDNA trace and identifies features in the electrical signal that reflect key sequences in the custom pT primer (labelled in FIG. 5 as—1=capture tail, 2=the iSpC3 spacers in the primer, 3=polyT primer for the reverse transcriptase and 4=region of cDNA). This example shows characterisation of cDNA which was transcribed from yeast (*Saccharomyces cerevisiae*) polyA+ mRNA as described in Example 1.

The invention claimed is:

1. A method of characterising a target ribonucleic acid (RNA) comprising a poly A tail, the method comprising:
   (a) forming a complementary polynucleotide from the target RNA by hybridising a primer to the poly A tail of the target RNA and using the primer to reverse transcribe the target RNA to form the complementary polynucleotide, wherein the primer comprises a leader sequence and/or a region to which a polynucleotide binding protein is capable of binding;
   (b) contacting the complementary polynucleotide with a transmembrane pore such that the complementary polynucleotide moves through the pore; and
   (c) taking one or more measurements as the complementary polynucleotide moves with respect to the pore wherein the measurements are indicative of one or more characteristics of the complementary polynucleotide and thereby characterising the target RNA,
   wherein the method does not comprise polymerase chain reaction (PCR) or reverse transcription PCR (RT-PCR), and
   wherein the complementary polynucleotide is contacted with the pore when the complementary polynucleotide is fully or partially hybridized to the targt RNA.

2. A method according to claim 1, wherein the target RNA is eukaryotic.

3. A method according to claim 1, wherein the primer is a polyT-VN primer, which comprises a polyT region and a VN anchor where V is dAMP, dCMP or dGMP and N is dAMP, dCMP, dGMP or dTMP.

4. A method according to claim 1, wherein the complementary polynucleotide is coupled to the membrane.

5. A method according to claim 1, wherein the one or more characteristics are selected from (i) the length of the target RNA, (ii) the identity of the target RNA, (iii) the sequence of the target RNA, and (iv) the amount of the target RNA.

6. A method according to claim 1, wherein the one or more characteristics of the complementary polynucleotide are measured by electrical measurement and/or optical measurement.

7. A method according to claim 6, wherein the electrical measurement is a current measurement, an impedance measurement, a tunnelling measurement or a field effect transistor (FET) measurement.

8. A method according to claim 1, wherein step (b) comprises contacting the complementary polynucleotide with a polynucleotide binding protein such that the protein controls the movement of the complementary polynucleotide through the pore.

9. A method according to claim 8, wherein the polynucleotide binding protein is a polymerase, exonuclease, helicase or a topoisomerase.

10. A method according to claim 1, wherein the method comprises
    (b) contacting the complementary polynucleotide with a transmembrane pore and a polynucleotide binding protein such that the protein controls the movement of the complementary polynucleotide through the pore; and
    (c) measuring the current passing through the pore as the complementary polynucleotide moves with respect to the pore wherein the current is indicative of one or more characteristics of the complementary polynucleotide and thereby characterising the template RNA.

11. A method according to claim 1, wherein the pore is a transmembrane protein pore or a solid state pore.

12. A method according to claim 11, wherein the transmembrane protein pore is derived from a hemolysin, leukocidin, *Mycobacterium smegmatis* porin A (MspA), MspB, MspC, MspD, outer membrane porin F (OmpF), outer membrane porin G (OmpG), outer membrane phospholipase A, *Neisseria* autotransporter lipoprotein (NalP) or WZA.

13. A method according to claim 12, wherein the transmembrane protein is:
   (a) formed of eight identical subunits as shown in SEQ ID NO: 2 or (b) a variant thereof in which one or more of the eight subunits has at least 50% homology to SEQ ID NO: 2 based on amino acid identity over the entire sequence and retains pore activity; or
   (c) formed of seven identical subunits as shown in SEQ ID NO: 4 or (d) a variant thereof in which one or more of the seven subunits has at least 50% homology to SEQ ID NO: 4 based on amino acid identity over the entire sequence and retains pore activity.

14. A method according to claim 1, wherein the target RNA is messenger RNA (mRNA) or microRNA (miRNA).

15. A method according to claim 14, wherein the mRNA or miRNA can be used to diagnose or prognose a disease or condition.

16. A method of determining whether or not a patient has or is at risk of developing a disease or condition associated with an altered amount and/or alternate splicing of messenger RNA (mRNA), comprising determining the amount and/or identity of the mRNA in a sample from the patient using a method according to claim 1 and thereby determining whether or not the patient has or is at risk of developing the disease or condition.

17. A method of characterising a target ribonucleic acid (RNA) comprising a polyA tail, comprising:
   (a) forming a complementary polynucleotide from the target RNA by hybridising a primer to the polyA tail of the target RNA and using the primer to reverse transcribe the target RNA to form the complementary polynucleotide;
   (b) contacting the complementary polynucleotide with a transmembrane pore such that the complementary polynucleotide moves through the pore; and
   (c) taking one or more measurements as the complementary polynucleotide moves with respect to the pore wherein the measurements are indicative of one or more characteristics of the complementary polynucleotide and thereby characterising the target RNA;
   wherein the complementary polynucleotide is contacted with the pore when the complementary polynucleotide is fully or partially hybridized to the target RNA.

18. A method according to claim 17, wherein the method does not comprise polymerase chain reaction (PCR) or reverse transcription PCR (RT-PCR).

19. A method according to claim 17, wherein the target RNA is eukaryotic.

20. A method according to claim 17, wherein the primer is a polyT-VN primer, which comprises a polyT region and a VN anchor where V is dAMP, dCMP or dGMP and N is dAMP, dCMP, dGMP or dTMP.

21. A method according to claim 17, wherein the complementary polynucleotide is coupled to the membrane.

22. A method according to claim 17 wherein the one or more characteristics are selected from (i) the length of the target RNA, (ii) the identity of the target RNA, (iii) the sequence of the target RNA, and (iv) the amount of the target RNA.

23. A method according to claim 17, wherein the one or more characteristics of the complementary polynucleotide are measured by electrical measurement and/or optical measurement.

24. A method according to claim 23, wherein the electrical measurement is a current measurement, an impedance measurement, a tunnelling measurement or a field effect transistor (FET) measurement.

25. A method according to claim 17, wherein step (b) comprises contacting the complementary polynucleotide with a polynucleotide binding protein such that the protein controls the movement of the complementary polynucleotide through the pore.

26. A method according to claim 25, wherein the polynucleotide binding protein is a polymerase, exonuclease, helicase or a topoisomerase.

27. A method according to claim 17, wherein the method comprises
   (b) contacting the complementary polynucleotide with a transmembrane pore and a polynucleotide binding protein such that the protein controls the movement of the complementary polynucleotide through the pore; and
   (c) measuring the current passing through the pore as the complementary polynucleotide moves with respect to the pore wherein the current is indicative of one or more characteristics of the complementary polynucleotide and thereby characterising the template RNA.

28. A method according to claim 17, wherein the pore is a transmembrane protein pore or a solid state pore.

29. A method according to claim 28, wherein the transmembrane protein pore is derived from a hemolysin, leukocidin, *Mycobacterium smegmatis* porin A (MspA), MspB, MspC, MspD, outer membrane porin F (OmpF), outer membrane porin G (OmpG), outer membrane phospholipase A, *Neisseria* autotransporter lipoprotein (NalP) or WZA.

30. A method according to claim 29, wherein the transmembrane protein is:
   (a) formed of eight identical subunits as shown in SEQ ID NO: 2 or (b) a variant thereof in which one or more of the eight subunits has at least 50% homology to SEQ ID NO: 2 based on amino acid identity over the entire sequence and retains pore activity; or
   (c) formed of seven identical subunits as shown in SEQ ID NO: 4 or (d) a variant thereof in which one or more of the seven subunits has at least 50% homology to SEQ ID NO: 4 based on amino acid identity over the entire sequence and retains pore activity.

31. A method according to claim 17, wherein the target RNA is messenger RNA (mRNA) or microRNA (miRNA).

32. A method according to claim 31, wherein the mRNA or miRNA can be used to diagnose or prognose a disease or condition.

33. A method of determining whether or not a patient has or is at risk of developing a disease or condition associated with an altered amount and/or alternate splicing of messenger RNA (mRNA), comprising determining the amount and/or identity of the mRNA in a sample from the patient using a method according to claim 17 and thereby determining whether or not the patient has or is at risk of developing the disease or condition.

\* \* \* \* \*

SEQUENCE LISTING

<160> NUMBER OF SEQ ID NOS: 13

<210> SEQ ID NO 1
<211> LENGTH: 558
<212> TYPE: DNA
<213> ORGANISM: Artificial sequence
<220> FEATURE:
<223> OTHER INFORMATION: MS-B1 mutant MspA monomer

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                    558
```

<210> SEQ ID NO 2
<211> LENGTH: 184
<212> TYPE: PRT
<213> ORGANISM: Artificial sequence
<220> FEATURE:
<223> OTHER INFORMATION: MS-B1 mutant MspA monomer

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45
```

```
Ile Val Ala Gly Pro Gly Ala Asp Glu Phe Glu Gly Thr Leu Glu Leu
 50                  55                  60
Gly Tyr Gln Ile Gly Phe Pro Trp Ser Leu Gly Val Gly Ile Asn Phe
 65                  70                  75                  80
Ser Tyr Thr Thr Pro Asn Ile Leu Ile Asn Asn Gly Asn Ile Thr Ala
                 85                  90                  95
Pro Pro Phe Gly Leu Asn Ser Val Ile Thr Pro Asn Leu Phe Pro Gly
             100                 105                 110
Val Ser Ile Ser Ala Arg Leu Gly Asn Gly Pro Gly Ile Gln Glu Val
             115                 120                 125
Ala Thr Phe Ser Val Arg Val Ser Gly Ala Lys Gly Val Ala Val
 130                 135                 140
Ser Asn Ala His Gly Thr Val Thr Gly Ala Ala Gly Val Leu Leu
 145                 150                 155                 160
Arg Pro Phe Ala Arg Leu Ile Ala Ser Thr Gly Asp Ser Val Thr Thr
                 165                 170                 175
Tyr Gly Glu Pro Trp Asn Met Asn
             180
```

<210> SEQ ID NO 3
<211> LENGTH: 885
<212> TYPE: DNA
<213> ORGANISM: Artificial sequence
<220> FEATURE:
<223> OTHER INFORMATION: alpha-hemolysin-E111N/K147N

<400> SEQUENCE: 3

```
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg tcaatatag agtttatagc gaagaaggtg ctaacaaaag tggtttagcc      240
tggccttcag cctttaaggt acagttgcaa ctacctgata tgaagtagc tcaaatatct      300
gattactatc aagaaattc gattgataca aaaaactata tgagtacttt aacttatgga      360
ttcaacggta atgttactgg tgatgataca ggaaaaattg gcggcttat tggtgcaaat      420
gtttcgattg tcatacact gaactatgtt caacctgatt tcaaaacaat tttagagagc      480
ccaactgata aaaagtagg ctggaaagtg atatttaaca atatggtgaa tcaaaattgg      540
ggaccatacg atcgagattc ttggaacccg gtatatggca atcaactttt catgaaaact      600
agaaatggtt ctatgaaagc agcagataac ttccttgatc ctaacaaagc aagttctcta      660
ttatcttcag ggttttcacc agacttcgct acagttatta ctatggatag aaaagcatcc      720
aaacaacaaa caaatataga gtaatatac gaacgagttc gtgatgatta ccaattgcat      780
tggacttcaa caaattggaa aggtaccaat actaaagata aatggacaga tcgttcttca      840
gaaagatata aaatcgattg ggaaaaagaa gaaatgacaa attaa                     885
```

<210> SEQ ID NO 4
<211> LENGTH: 293
<212> TYPE: PRT
<213> ORGANISM: Artificial sequence
<220> FEATURE:
<223> OTHER INFORMATION: alpha-hemolysin-E111N/K147N

<400> SEQUENCE: 4

```
Ala Asp Ser Asp Ile Asn Ile Lys Thr Gly Thr Thr Asp Ile Gly Ser
 1               5                  10                  15
```

```
Asn Thr Thr Val Lys Thr Gly Asp Leu Val Thr Tyr Asp Lys Glu Asn
             20                  25                  30

Gly Met His Lys Lys Val Phe Tyr Ser Phe Ile Asp Lys Asn His
         35                  40                  45

Asn Lys Lys Leu Leu Val Ile Arg Thr Lys Gly Thr Ile Ala Gly Gln
     50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Asn Tyr
                100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
```

```
                    85                  90                  95
Pro Pro Phe Gly Leu Asn Ser Val Ile Thr Pro Asn Leu Phe Pro Gly
                100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
                180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
                100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
                180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
                20                  25                  30

Asn Arg Leu Thr Arg Glu Trp Phe His Ser Gly Arg Ala Thr Tyr His
```

```
            35                  40                  45
Val Ala Gly Pro Gly Ala Asp Glu Phe Glu Gly Thr Leu Glu Leu Gly
 50                  55                  60

Tyr Gln Val Gly Phe Pro Trp Ser Leu Gly Val Gly Ile Asn Phe Ser
 65                  70                  75                  80

Tyr Thr Thr Pro Asn Ile Leu Ile Asp Gly Asp Ile Thr Gln Pro
                 85                  90                  95

Pro Phe Gly Leu Asp Thr Ile Ile Thr Pro Asn Leu Phe Pro Gly Val
                100                 105                 110

Ser Ile Ser Ala Asp Leu Gly Asn Gly Pro Gly Ile Gln Glu Val Ala
                115                 120                 125

Thr Phe Ser Val Asp Val Lys Gly Ala Lys Gly Ala Val Ala Val Ser
                130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
                180

<210> SEQ ID NO 8
<211> LENGTH: 90
<212> TYPE: RNA
<213> ORGANISM: Artificial sequence
<220> FEATURE:
<223> OTHER INFORMATION: mRNA sequence analysed in the Examples

<400> SEQUENCE: 8
guaucuccau cgcugauuag agaaauacaa agaacaaaca aucgggcacc agaacaaagg      60
ucguagugcu aaaaaaaaaa aaaaaaaaaa                                      90

<210> SEQ ID NO 9
<211> LENGTH: 47
<212> TYPE: DNA
<213> ORGANISM: Artificial sequence
<220> FEATURE:
<223> OTHER INFORMATION: Primer sequence used in the Examples

<400> SEQUENCE: 9 cccccccca cccccccca cccccccca cccccccca ccccccc                       47

<210> SEQ ID NO 10
<211> LENGTH: 52
<212> TYPE: DNA
<213> ORGANISM: Artificial sequence
<220> FEATURE:
<223> OTHER INFORMATION: Primer sequence used in the Examples
<220> FEATURE:
<221> NAME/KEY: misc_feature
<222> LOCATION: (51)..(51)
<223> OTHER INFORMATION: n is a, c, or g
<220> FEATURE:
<221> NAME/KEY: misc_feature
<222> LOCATION: (52)..(52)
<223> OTHER INFORMATION: n is a, c, g, or t

<400> SEQUENCE: 10
ggttgtttct gttggtgctg atattgcttt ttttttttt tttttttttt nn             52

<210> SEQ ID NO 11
<211> LENGTH: 70
<212> TYPE: DNA
```

<213> ORGANISM: Artificial sequence
<220> FEATURE:
<223> OTHER INFORMATION: cDNA transcribed in the Examples

<400> SEQUENCE: 11
agcactacga cctttgttct ggtgcccgat tgtttgttct ttgtatttct ctaatcagcg    60
atggagatac                                                          70

<210> SEQ ID NO 12
<211> LENGTH: 28
<212> TYPE: DNA
<213> ORGANISM: Artificial sequence
<220> FEATURE:
<223> OTHER INFORMATION: Tether sequence used in the Examples

<400> SEQUENCE: 12
gcaatatcag caccaacaga aacaacct                                       28

<210> SEQ ID NO 13
<211> LENGTH: 439
<212> TYPE: PRT
<213> ORGANISM: Bacteriophage T4

<400> SEQUENCE: 13

Met Thr Phe Asp Asp Leu Thr Glu Gly Gln Lys Asn Ala Phe Asn Ile
1               5                   10                  15

Val Met Lys Ala Ile Lys Glu Lys Lys His Val Thr Ile Asn Gly
            20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His
    50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
        115                 120                 125

Leu Ser Thr Ile Pro Pro Trp Cys Thr Ile Ile Gly Ile Gly Asp Asn
    130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln

-continued

```
                      260                 265                 270
Glu Pro Leu Phe Lys Thr Tyr Lys Ile Asp Gly Lys Pro Val Ser Glu
            275                 280                 285

Ile Ile Phe Asn Asn Gly Gln Leu Val Arg Ile Ile Glu Ala Glu Tyr
        290                 295                 300

Thr Ser Thr Phe Val Lys Ala Arg Gly Val Pro Gly Glu Tyr Leu Ile
305                 310                 315                     320

Arg His Trp Asp Leu Thr Val Glu Thr Tyr Gly Asp Asp Glu Tyr Tyr
            325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
            355                 360                 365

Gly Gly Lys Ala Pro Trp Ser Asp Phe Trp Asp Ala Lys Ser Gln Phe
        370                 375                 380

Ser Lys Val Lys Ala Leu Pro Ala Ser Thr Phe His Lys Ala Gln Gly
385                 390                 395                     400

Met Ser Val Asp Arg Ala Phe Ile Tyr Thr Pro Cys Ile His Tyr Ala
            405                 410                 415

Asp Val Glu Leu Ala Gln Gln Leu Leu Tyr Val Gly Val Thr Arg Gly
            420                 425                 430

Arg Tyr Asp Val Phe Tyr Val
        435
```